US009545222B2

(12) United States Patent
Derchak et al.

(10) Patent No.: US 9,545,222 B2
(45) Date of Patent: Jan. 17, 2017

(54) GARMENT WITH NONINVASIVE METHOD AND SYSTEM FOR MONITORING PHYSIOLOGICAL CHARACTERISTICS AND ATHLETIC PERFORMANCE

(75) Inventors: P. Alexander Derchak, Oxnard, CA (US); George McLean, Mountain View, CA (US)

(73) Assignee: adidas AG, Herzogenaurach (DE)

( * ) Notice: Subject to any disclaimer, the term of this patent is extended or adjusted under 35 U.S.C. 154(b) by 413 days.

(21) Appl. No.: 12/869,582

(22) Filed: Aug. 26, 2010

(65) Prior Publication Data

US 2011/0130643 A1    Jun. 2, 2011

Related U.S. Application Data

(60) Provisional application No. 61/275,574, filed on Sep. 1, 2009, provisional application No. 61/275,575, filed on
(Continued)

(51) Int. Cl.
*A61B 5/0205* (2006.01)
*A61B 5/113* (2006.01)
(Continued)

(52) U.S. Cl.
CPC ........... *A61B 5/1135* (2013.01); *A61B 5/0002* (2013.01); *A61B 5/02055* (2013.01);
(Continued)

(58) Field of Classification Search
USPC ........................................................ 600/409
See application file for complete search history.

(56) References Cited

U.S. PATENT DOCUMENTS 3,831,586 A    8/1974 Petit
4,033,332 A    7/1977 Hardway et al.
(Continued)

FOREIGN PATENT DOCUMENTS

JP    3-501554 A    4/1991
JP    5-91511 A    4/1993
(Continued)

OTHER PUBLICATIONS

Clarenbach et al. (Monitoring of Ventilation During Exercise by a Portable Respiratory Inductive Plethysmograph, Chest, 2005; 128:1282-1290).*
(Continued)

*Primary Examiner* — Serkan Akar
(74) *Attorney, Agent, or Firm* — Sterne, Kessler, Goldstein & Fox P.L.L.C.

(57) ABSTRACT

A physiological monitoring system for noninvasively monitoring physiological parameters of a subject, comprising a fitness monitoring system for monitoring physiological parameters of a subject engaged in a physical activity, in accordance with one embodiment of the invention, includes (i) a monitoring garment adapted to cover at least a portion of a subject's torso, (ii) a magnetometer subsystem including a first magnetometer and a second magnetometer, wherein the first and second magnetometers are responsive to changes in distance therebetween, wherein the magnetometer subsystem is configured to generate and transmit a signal representative of a change in the distance between the first and second magnetometers, wherein the first and second magnetometers are incorporated into the monitoring garment, and wherein the first and second magnetometers are proximate to the subject's chest region when the monitoring garment is worn by the subject.

51 Claims, 8 Drawing Sheets

Related U.S. Application Data on Sep. 1, 2009, provisional application No. 61/275,586, filed on Sep. 1, 2009, provisional application No. 61/275,587, filed on Sep. 1, 2009, provisional application No. 61/275,633, filed on Sep. 1, 2009, provisional application No. 61/275,634, filed on Sep. 1, 2009, provisional application No. 61/275,635, filed on Sep. 1, 2009.

(51) Int. Cl.
| | | |
|---|---|---|
| A61B 5/00 | (2006.01) | |
| G06F 19/00 | (2011.01) | |
| A61B 5/024 | (2006.01) | |
| A61B 5/0402 | (2006.01) | |
| A61B 5/0476 | (2006.01) | |
| A61B 5/11 | (2006.01) | |
| A61B 5/1455 | (2006.01) | |
| A61B 7/00 | (2006.01) | |

(52) U.S. Cl.
CPC ........ *A61B 5/6805* (2013.01); *G06F 19/3481* (2013.01); *A61B 5/02438* (2013.01); *A61B 5/0402* (2013.01); *A61B 5/0476* (2013.01); *A61B 5/11* (2013.01); *A61B 5/14551* (2013.01); *A61B 5/411* (2013.01); *A61B 7/003* (2013.01); *A61B 2562/0219* (2013.01)

(56) References Cited

U.S. PATENT DOCUMENTS

| | | | |
|---|---|---|---|
| 4,258,718 A | | 3/1981 | Goldman |
| 4,267,845 A | | 5/1981 | Robertson, Jr. et al. |
| 4,494,553 A | | 1/1985 | Sciarra et al. |
| 5,002,060 A | | 3/1991 | Nedivi |
| 5,148,002 A | * | 9/1992 | Kuo et al. ................ 219/211 |
| 5,255,318 A | | 10/1993 | Gurusami et al. |
| 5,549,113 A | | 8/1996 | Halleck et al. |
| 5,738,102 A | | 4/1998 | Lemelson |
| 5,825,293 A | | 10/1998 | Ahmed et al. |
| 5,906,004 A | | 5/1999 | Lebby et al. |
| 6,015,388 A | | 1/2000 | Sackner et al. |
| 6,047,203 A | | 4/2000 | Sackner et al. |
| 6,080,690 A | | 6/2000 | Lebby et al. |
| 6,198,394 B1 | | 3/2001 | Jacobsen et al. |
| 6,268,725 B1 | | 7/2001 | Vernon et al. |
| 6,341,504 B1 | | 1/2002 | Istook |
| 6,450,957 B1 | | 9/2002 | Yoshimi et al. |
| 6,454,719 B1 | | 9/2002 | Greenhut |
| 6,468,234 B1 | | 10/2002 | Van der Loos et al. |
| 6,517,497 B2 | | 2/2003 | Rymut et al. |
| 6,527,729 B1 | | 3/2003 | Turcott |
| 6,551,252 B2 | | 4/2003 | Sackner et al. |
| 6,599,251 B2 | | 7/2003 | Chen et al. |
| 6,600,949 B1 | | 7/2003 | Turcott |
| 6,727,197 B1 | | 4/2004 | Wilson et al. |
| 6,790,183 B2 | | 9/2004 | Murphy |
| 6,840,907 B1 | | 1/2005 | Brydon |
| 6,858,006 B2 | | 2/2005 | MacCarter et al. |
| 7,267,262 B1 | | 9/2007 | Brown |
| 7,267,652 B2 | | 9/2007 | Coyle et al. |
| 7,295,928 B2 | | 11/2007 | Hassan et al. |
| 2002/0123701 A1 | | 9/2002 | Eriksen et al. |
| 2004/0097823 A1 | | 5/2004 | Friedrichs et al. |
| 2004/0117204 A1 | | 6/2004 | Mazar et al. |
| 2004/0122334 A1 | | 6/2004 | Yamashiro |
| 2004/0133079 A1 | | 7/2004 | Mazar |
| 2005/0054941 A1 | | 3/2005 | Ting |
| 2005/0119586 A1 | * | 6/2005 | Coyle et al. ................ 600/538 |
| 2007/0169364 A1 | | 7/2007 | Townsend et al. |
| 2007/0270689 A1 | | 11/2007 | Lothert |
| 2007/0287896 A1 | | 12/2007 | Derchak et al. |
| 2008/0039700 A1 | | 2/2008 | Drinan et al. |
| 2008/0045815 A1 | | 2/2008 | Derchak et al. |
| 2008/0082018 A1 | | 4/2008 | Sackner et al. |
| 2008/0223131 A1 | | 9/2008 | Vannucci et al. |
| 2008/0269644 A1 | | 10/2008 | Ray |
| 2008/0312547 A1 | | 12/2008 | Wada |
| 2008/0312709 A1 | | 12/2008 | Volpe et al. |
| 2009/0047645 A1 | | 2/2009 | DiBenedetto et al. |
| 2010/0027515 A1 | | 2/2010 | Hylton |
| 2010/0234699 A1 | | 9/2010 | Lanfermann et al. |
| 2010/0292050 A1 | | 11/2010 | DiBenedetto et al. |
| 2011/0009766 A1 | * | 1/2011 | McCool ................ 600/534 |
| 2011/0153701 A1 | | 6/2011 | Moudgill |

FOREIGN PATENT DOCUMENTS

| | | |
|---|---|---|
| JP | 09-028661 A | 2/1997 |
| JP | 2003-513260 A | 4/2003 |
| JP | 2005-184188 A | 7/2005 |
| JP | 2006-208291 A | 8/2006 |
| JP | 2007-125360 A | 5/2007 |
| JP | 2008-229084 A | 10/2008 |
| JP | 2008-307382 A | 12/2008 |
| WO | 89/05549 A1 | 6/1989 |
| WO | WO 01/28420 A1 | 4/2001 |
| WO | 01/33162 A1 | 5/2001 |
| WO | WO 01/76467 A2 | 10/2001 |
| WO | WO 2004/016009 A1 | 2/2004 |
| WO | WO 2006/002338 A2 | 1/2006 |
| WO | WO 2006/009830 A2 | 1/2006 |
| WO | WO 2006/034291 A2 | 3/2006 |
| WO | WO 2006/127573 A2 | 11/2006 |
| WO | WO 2007/069111 A2 | 6/2007 |
| WO | WO 2009/074973 A1 | 6/2009 |

OTHER PUBLICATIONS

Noury et al. (VTAMN A Smart Clothe for Ambulatory Remote Monitoring of Physiological Parameters and Activity, IEEE EMBS, 2004).*

McCool et al, Tidal Volume and Respiratory Timing Derived From a Portable Ventilation Monitor (Chest 2002; 122:684-691).*

Badler, et al., "Simulating Humans: Computer Graphics, Animation, and Control", (New York: Oxford University Press, 1993).

DeCarlo, et al., "Integrating Anatomy and Physiology for Behavior Modeling", Medicine Meets Virtual Reality 3 (San Diego, 1995).

McCool, et al., "Estimates of Ventilation From Body Surface Measurements in Unrestrained Subjects", J. Appl. Physiol., vol. 61, pp. 1114-1119 (1986).

Mead, et al., "Pulmonary Ventilation Measured from Body Surface Movements", Science, pp. 196, 1383-1384 (1967).

Paek, et al., "Postural Effects on Measurements of Tidal Volume From Body Surface Displacements", J. Appl. Physiol., vol. 68, pp. 2482-2487 (1990).

Smith, et al., "Three Degree of Freedom Description of Movement of the Human Chest Wall", J. Appl. Physiol., vol. 60, pp. 928-934 (1986).

Wade, O.L., "Movements of the Thoracic Cage and Diaphragm in Respiration", J. Physiol., pp. 124-193 (1954).

Co-pending U.S. Appl. No. 12/869,578, inventors Derchak et al., filed Aug. 26, 2010.

Co-pending U.S. Appl. No. 12/869,576, inventor Stone, Robert, filed Aug. 26, 2010.

Co-pending U.S. Appl. No. 12/869,585, inventor Derchak, P. Alexander, filed Aug. 26, 2010.

Co-pending U.S. Appl. No. 12/869,592, inventor Derchak, P. Alexander, filed Aug. 26, 2010.

Co-pending U.S. Appl. No. 12/872,174, inventor Derchak et al., filed Aug. 31, 2010.

Co-pending U.S. Appl. No. 12/869,625, inventor Derchak, P. Alexander, filed Aug. 26, 2010.

Co-pending U.S. Appl. No. 12/869,586, inventor Derchak et al., filed Aug. 26, 2010.

Co-pending U.S. Appl. No. 12/836,421, inventors Powch, et al., filed Jul. 14, 2010.

Office Action mailed Aug. 30, 2012 for U.S. Appl. No. 12/869,578.

(56) References Cited

OTHER PUBLICATIONS

Office Action mailed Sep. 21, 2012 for U.S. Appl. No. 12/869,585.
Office Action mailed Mar. 19, 2013 for U.S. Appl. No. 12/869,578.
Office Action mailed Jan. 14, 2013 for U.S. Appl. No. 12/869,585.
D'Angelo, 30th Annual International IEEE EMBS Conference, Aug. 20-24, 2008, pp. 3694-3697.
Office Action mailed Mar. 24, 2014 for U.S. Appl. No. 12/869,585.
Office Action for Japanese Application No. 2010-196119 dated Jul. 1, 2014, "Notice of Reasons for Rejection," Mailing Date: Jul. 1, 2014, 7 pages.

* cited by examiner

GARMENT WITH NONINVASIVE METHOD AND SYSTEM FOR MONITORING PHYSIOLOGICAL CHARACTERISTICS AND ATHLETIC PERFORMANCE

CROSS-REFERENCE TO RELATED APPLICATIONS

This non-provisional application claims priority to U.S. Provisional Application No. 61/275,574, filed Sep. 1, 2009, U.S. Provisional Application No. 61/275,575, filed Sep. 1, 2009, U.S. Provisional Application No. 61/275,586, filed Sep. 1, 2009, U.S. Provisional Application No. 61/275,587, filed Sep. 1, 2009, U.S. Provisional Application No. 61/275,633, filed Sep. 1, 2009, U.S. Provisional Application No. 61/275,634, filed Sep. 1, 2009, and U.S. Provisional Application No. 61/275,635, filed Sep. 1, 2009, each of which is incorporated herein by reference in its entirety.

FIELD OF THE INVENTION

The present invention relates generally to methods and systems for monitoring physiological and athletic performance characteristics of a subject. More particularly, the invention relates to improved methods and systems for determining a plurality of physiological and athletic performance characteristics and characterizing respiratory activity and associated events, as well as spatial parameters, in real-time. The methods and systems of the present invention can be applied in a variety of fields, e.g., health care, medical diagnosis and monitoring, and athletic monitoring and coaching.

BACKGROUND OF THE INVENTION

In medical diagnosis and treatment of a subject, it is often necessary to assess one or more physiological characteristics, particularly respiratory characteristics. A key respiratory characteristic is respiratory air volume (or tidal volume). Respiratory air volume and other respiratory characteristics are also useful to assess athletic performance, for example, by aiding in detection of changes in physiological state and/or performance characteristics.

Monitoring physiological and performance parameters of a subject can be important in planning and evaluating athletic training and activity. A subject may exercise or otherwise engage in athletic activity for a variety of reasons, including, for example, maintaining or achieving a level of fitness, to prepare for or engage in competition, and for enjoyment. The subject may have a training program tailored to his or her fitness level and designed to help him or her progress toward a fitness or exercise goal. Physiological and performance parameters of a subject can provide useful information about the subject's progression in a training program, or about the athletic performance of the subject. In order to accurately appraise the subject's fitness level or progress toward a goal, it may be useful to determine, monitor, and record various physiological or performance parameters, and related contextual information.

In the past, various methods and systems utilizing heart rate have been introduced to approximate effort and physiological stress during exercise. However, convenient, practicable, and comfortable means of measuring pulmonary ventilation in non-laboratory conditions have been scarce. While of good value, heart rate can only give an approximation as to the true physiological state of an athlete or medical patient, as it can be confounded by external factors including, for example, sleep levels, caffeine, depressants, beta blockers, stress levels, hydration status, temperature, etc. Furthermore, accurate use of heart rate to gauge physiological performance requires knowledge of the amount of blood flowing to the muscles, which in turn requires knowledge of the instantaneous stroke volume of the heart as well as the rate of pumping. These parameters can be difficult to determine while a subject is engaging in a physical activity.

Various conventional methods and systems have been employed to measure (or determine) tidal volume. One method comprises having the patient or subject breathe into a mouthpiece connected to a flow rate measuring device. Flow rate is then integrated to provide air volume change.

As is well known in the art, there are several drawbacks and disadvantages associated with employing a mouthpiece. A significant drawback associated with a mouthpiece and nose-clip measuring device is that the noted items cause changes in the monitored subject's respiratory pattern (i.e., rate and volume). Tidal volume determinations based on a mouthpiece and nose-clip are, thus, often inaccurate.

A mouthpiece is difficult to use for monitoring athletic performance as we as for long term monitoring, especially for ill, sleeping or anesthetized subjects. It is uncomfortable for the subject, tends to restrict breathing, and is generally inconvenient for the physician or technician to use. Monitoring respiratory characteristics using a mouthpiece is particularly impractical in the athletic performance monitoring context. During athletic activities, the mouthpiece interferes with the athlete's performance. The processing and collection accessories necessary to monitor the breathing patterns captured by the mouthpiece add further bulk to such devices. These systems also typically require an on-duty technician to set up and operate, further complicating their use.

Another conventional device for determining tidal volume includes respiration monitors. Illustrative are the systems disclosed in U.S. Pat. No. 3,831,586, issued Aug. 27, 1974, and U.S. Pat. No. 4,033,332, issued Jul. 5, 1977, each of which is incorporated by reference herein in its entirety.

Although the noted systems eliminate most of the disadvantages associated with a mouthpiece, the systems do not, in general, provide an accurate measurement of tidal volume. Further, the systems are typically only used to signal an attendant when a subject's breathing activity changes sharply or stops.

A further means for determining tidal volume is to measure the change in size (or displacement) of the rib cage and abdomen, as it is well known that lung volume is a function of these two parameters. A number of systems and devices have been employed to measure the change in size (i.e., $\Delta$ circumference) of the rib cage and abdomen, including mercury in rubber strain gauges, pneumobelts, respiratory inductive plethysmograph (RIP) belts and magnetometers. See, D. L. Wade, "*Movements of the Thoracic Cage and Diaphragm in Respiration*", J. Physiol., pp. 124-193 (1954), Mead, et al. "*Pulmonary Ventilation Measured from Body Surface Movements*", Science, pp. 196, 1383-1384 (1967).

RIP belts are a common means employed to measure changes in the cross-sectional areas of the rib cage and abdomen. RIP belts comprise conductive loops of wire that are coiled and sewed into an elastic belt. As the coil stretches and contracts in response to changes in a subject's chest cavity size, a magnetic field generated by the wire changes. The output voltage of an RIP belt is generally linearly related to changes in the expanded length of the belt and, thus, changes in the enclosed cross-sectional area.

In practice, measuring changes in the cross-sectional areas of the abdomen can increase the accuracy of RIP belt systems. To measure changes in the cross-sectional areas of the rib cage and abdomen, one belt is thus typically secured around the mid-thorax and a second belt is placed around the mid-abdomen.

RIP belts can also be embedded in a garment, such as a shirt or vest, and appropriately positioned therein to measure rib cage and abdominal displacements, and other anatomical and physiological parameters, such as jugular venous pulse, respiration-related intra-plural pressure changes, etc. Illustrative is the VivoMetrics, Inc. LifeShirt® disclosed in U.S. Pat. No. 6,551,252, issued Apr. 22, 2003 and U.S. Pat. No. 6,341,504, issued Jan. 29, 2002, each of which is incorporated by reference herein in its entirety.

However, there are some drawbacks to many RIP belt systems. For example, RIP belts are expensive in terms of material construction and in terms of the electrical and computing power required to operate them. In addition, the coils are generally large and tight on the chest and therefore can be cumbersome and uncomfortable for the athlete.

Other technologies have been developed in an attempt to monitor respiratory characteristics of a subject while avoiding the drawbacks of RIP belt systems. These technologies generally work on a strain gauge principle and are often textile based. However, such technologies suffer significantly from motion interference that, by and large, renders them useless in athletic training applications where motion is necessarily at a relatively high level.

In an attempt to rectify the drawbacks of the RIP belt and strain gauge systems, various magnetometer systems have been recently developed to measure displacements of the rib cage and abdomen. Respiratory magnetometer systems typically comprise one or more tuned pairs of air-core magnetometers or electromagnetic coils. Other types of magnetometers sensitive to changes in distance therebetween can also be used. One magnetometer is adapted to transmit a specific high frequency AC magnetic field and the other magnetometer is adapted to receive the field. The paired magnetometers are responsive to changes in a spaced distance therebetween; the changes being reflected in changes in the strength of the magnetic field.

To measure changes in (or displacement of) the anteroposterior diameter of the rib cage, a first magnetometer is typically placed over the sternum at the level of the 4th intercostal space and the second magnetometer is placed over the spine at the same level. Using additional magnetometers can increase the accuracy of the magnetometer system. For example, to measure changes in the anteroposterior diameter of the abdomen, a third magnetometer can be placed on the abdomen at the level of the umbilicus and a fourth magnetometer can be placed over the spine at the same level.

Over the operational range of distances, the output voltage is linearly related to the distance between two magnetometers provided that the axes of the magnetometers remain substantially parallel to each other. As rotation of the axes can change the voltage, the magnetometers are typically secured to the subject's skin in a parallel fashion and rotation due to the motion of underlying soft tissue is minimized.

Various methods, algorithms and mathematical models have been employed with the aforementioned systems to determine tidal volume and other respiratory characteristics. In practice, "two-degrees-of-freedom" models are typically employed to determine tidal volume from RIP belt derived rib cage and abdominal displacements.

The "two-degrees-of-freedom" models are premised on the inter-related movements by and between the thoracic cavity and the anterior and lateral walls of the rib cage and the abdomen, i.e., since the first rib and adjacent structures of the neck are relatively immobile, the moveable components of the thoracic cavity are taken to be the anterior and lateral walls of the rib cage and the abdomen. Changes in volume of the thoracic cavity will then be reflected by displacements of the rib cage and abdomen.

As is well known in the art, displacement (i.e., movement) of the rib cage can be directly assessed with an RIP belt. Diaphragm displacement cannot, however, be measured directly. But, since the abdominal contents are essentially incompressible, caudal motion of the diaphragm relative to the pelvis and the volume it displaces is reflected by outward movement of the anterolateral abdominal wall.

The "two-degrees-of-freedom" model embraced by many in the field holds that tidal volume ($V_T$) is equal to the sum of the volume displacements of the rib cage and abdomen, i.e.:

$$V_T = \alpha RC + \beta Ab \qquad \text{Eq. 1}$$

where RC and Ab represent linear displacements of the rib cage and abdomen, respectively; and $\alpha$ and $\beta$ represent volume-motion coefficients.

The accuracy of the "two-degrees-of-freedom" model and, hence, methods employing same to determine volume-motion coefficients of the rib cage and abdomen, is limited by virtue of changes in spinal flexion that can accompany changes in posture. Indeed, it has been found that $V_T$ can be over or under-estimated by as much as 50% of the vital capacity with spinal flexion and extension. See, McCool, et al., "*Estimates of Ventilation From Body Surface Measurements in Unrestrained Subjects*", J. Appl. Physiol., vol. 61, pp. 1114-1119 (1986) and Paek, et al., "*Postural Effects on Measurements of Tidal Volume From Body Surface Displacements*", J. Appl. Physiol., vol. 68, pp. 2482-2487 (1990).

There are two major causes that contribute to the noted error and, hence, limitation. A first contributing cause of the error is due to the substantial displacement of the summed rib cage and abdomen signals that occurs with isovolume spinal flexion and extension or pelvic rotation.

The second contributing cause of the error is due to posturally-induced changes in volume-motion coefficients. With isovolume spinal flexion, the rib cage comes down with respect to the pelvis and the axial dimension of the anterior abdominal wall becomes smaller. Therefore, less abdominal cavity is bordered by the anterior abdominal wall With a smaller anterior abdominal wall surface to displace, a given volume displacement of the abdominal compartment would be accompanied by a greater outward displacement of the anterior abdominal wall. The abdominal volume-motion coefficient would accordingly be reduced.

It has, however, been found that the addition of a measure of the axial motion of the chest wall, e.g., changes in the distance between the xiphoid and the pubic symphysis (Xi), provides a third degree of freedom, which, when employed to determine tidal volume ($V_T$) can reduce the posture related error associated with the "two-degrees-of-freedom" model to within 15% of that measured by spirometry. See, Paek, et al., "*Postural Effects on Measurements of Tidal Volume From Body Surface Displacements*", J. Appl. Physiol., vol. 68, pp. 2482-2487 (1990); and Smith, et al. "*Three Degree of Freedom Description of Movement of the Human Chest Wall*", J. Appl. Physiol., Vol. 60, pp. 928-934 (1986).

Several magnetometer systems are thus adapted to additionally measure the displacement of the chest wall. Illustrative are the magnetometer systems disclosed in co-pending U.S. patent application Ser. No. 12/231,692, filed Sep. 5, 2008, which is incorporated by reference herein in its entirety.

Various methods, algorithms and models are similarly employed with the magnetometer systems to determine tidal volume (Vr) and other respiratory characteristics based on measured displacements of the rib cage, abdomen and chest wall. The model embraced by many in the field is set forth in Equation 2 below:

$$V_T = \alpha(\Delta RC) + \beta(\Delta ab) + \gamma(\Delta Xi) \quad \text{Eq. 2}$$

where:

$\Delta RC$) represents the linear displacement of the rib cage;
$\Delta Ab$ represents the linear displacement of the abdomen;
$\Delta Xi$ represents axial displacement of the chest wall;
$\alpha$ represents a rib cage volume-motion coefficient;
$\beta$ represents an abdominal volume-motion coefficient; and
$\gamma$ represents a chest wall volume-motion coefficient.

There are, however, similarly several drawbacks and disadvantages associated with the noted "three-degrees-of-freedom" model. A major drawback is that posture related errors in tidal volume determinations are highly probable when a subject is involved in freely moving postural tasks, e.g., bending, wherein spinal flexion and/or extension is exhibited.

The most pronounced effect of spinal flexion is on the abdominal volume-motion coefficient ($\beta$). With bending, $\beta$ decreases as the xiphi-umbilical distance decreases.

Various approaches and models have thus been developed to address the noted dependency and, hence, enhance the accuracy of tidal volume ($V_T$) determinations. In co-pending U.S. patent application Ser. No. 12/231,692, a modified "three-degrees-of-freedom" model is employed to address the dependence of $\beta$ on the xiphi-umbilical distance, i.e., $$V_T = \alpha(\Delta RC) + \beta_u + \epsilon Xi0 \times (\Delta Ab) + \gamma(\Delta Xi) \quad \text{Eq. 3}$$

where:

$\Delta RC$ represents the linear displacement of the rib cage;
$\Delta Ab$ represents the linear displacement of the abdomen;
$\Delta Xi$ represents the change in the xiphi-umbilical distance from an upright position;
$\alpha$ represents a rib cage volume-motion coefficient;
$\beta$ represents an abdominal volume-motion coefficient;
$\beta_u$ represents the value of the abdominal volume-motion coefficient ($\beta$) in the upright position;
$\epsilon$ represents the linear slope of the relationship of $\beta$ as a function of the xiphi-umbilical distance Xi:
($\beta_u + \epsilon Xi$) represents the corrected abdominal volume-motion coefficient; and
$\gamma$ represents a xiphi-umbilical volume-motion coefficient.

The "three-degrees-of-freedom" model reflected in Equation 3 above and the associated magnetometer systems and methods disclosed in co-pending U.S. patent application Ser. No. 12/231,692 have been found to reduce the posture related error(s) in tidal volume ($V_T$) and other respiratory characteristic determinations. There are, however, several issues with the disclosed magnetometer systems and methods. One issue is that the magnetometer systems require complex calibration algorithms and associated techniques to accurately determine tidal volume ($V_T$) and other respiratory characteristics. A further issue, which is discussed in detail herein, is that the chest wall and respiratory data provided by the disclosed systems (and associated methods) is limited and, hence, limits the scope of respiratory characteristics and activity determined therefrom.

BRIEF SUMMARY OF THE INVENTION

The present invention provides apparatuses and methods for improved monitoring of a subject's respiratory characteristics, which is of particular use in the fields of athletic performance monitoring and medical evaluation. In accordance with the above objects and those that will be mentioned and will become apparent below, a fitness monitoring system for monitoring physiological parameters of a subject engaged in a physical activity, in accordance with one embodiment of the invention, includes (i) a monitoring garment adapted to cover at least a portion of a subject's torso, (ii) a magnetometer subsystem including a first magnetometer and a second magnetometer, wherein the first and second magnetometers are responsive to changes in distance therebetween, wherein the magnetometer subsystem is configured to generate and transmit a signal representative of a change in the distance between the first and second magnetometers, wherein the first and second magnetometers are incorporated into the monitoring garment, and wherein the first and second magnetometers are proximate to the subject's chest region when the monitoring garment is worn by the subject. The fitness monitoring system can also include a processor subsystem in communication with the magnetometer subsystem and configured to receive the signal, wherein the processor subsystem is programmed and adapted to control the magnetometer subsystem and to process the signal, wherein the processor subsystem includes an empirical relationship for determining a respiratory characteristic from the signal, and wherein the processor subsystem is adapted to generate and transmit a respiratory characteristic signal representative of the respiratory characteristic.

The monitoring system can also be adapted to measure and/or calculate various performance parameters associated with the athlete's physical activity, as explained in further detail below.

The monitoring system may include or communicate with one or more sensors for detecting information used to measure and/or calculate performance parameters. Suitable sensors may include, for example, the sensors disclosed in commonly owned U.S. patent application Ser. No. 11/892,023, filed Aug. 17, 2007, titled "Sports Electronic Training System, and Applications Thereof", commonly owned U.S. patent application Ser. No. 12/467,944, filed May 18, 2009, titled "Portable Fitness Monitoring Systems, and Applications Thereof", and commonly owned U.S. patent application Ser. No. 12/836,421, filed Jul. 14, 2010, titled "Fitness Monitoring Methods, Systems, and Program Products, and Applications Thereof", each of which is incorporated by reference herein in its entirety.

In accordance with another embodiment of the invention, the fitness monitoring system for monitoring physiological parameters of a subject engaged in a physical activity includes (i) a wearable monitoring garment, the monitoring garment being adapted to cover at least a portion of a subject's torso, and (ii) a magnetometer subsystem including a first magnetometer and a second magnetometer, wherein the first and second magnetometers are responsive to changes in distance therebetween, wherein the magnetometer subsystem is configured to generate and transmit magnetometer signals representative of a change in the distance between the first and second magnetometers, wherein the first and second magnetometers are incorporated into the monitoring garment, wherein, when the monitoring garment is worn by the subject, the first and second magnetometers are disposed proximate the subject's chest region. The fitness monitoring system can further include a processor subsystem in communication with the magnetometer subsystem, the processor subsystem being programmed and adapted to control at least the magnetometer subsystem, the processor subsystem being further adapted to receive and process the magnetometer signals, wherein the processor subsystem includes an empirical relationship for determining a respiratory characteristic from the magnetometer signals, and further programmed and adapted to generate and transmit a respiratory characteristic signal representing the respiratory characteristic. A data monitoring subsystem can be provided that is programmed and adapted to receive the respiratory characteristic signal, the data monitoring subsystem being programmed to recognize and display the respiratory characteristic associated with the respiratory characteristic signal.

In accordance with another embodiment of the invention, the monitoring system for noninvasively monitoring physiological parameters of a subject, in accordance with one embodiment of the invention, generally comprises (i) a wearable monitoring garment that is adapted to cover at least a portion of a subject's torso, and (ii) a magnetometer system, the magnetometer system being embedded in the monitoring garment, the magnetometer system including magnetometers that are responsive to changes in distance therebetween, the magnetometer system being adapted to generate at least one signal representing changes in the distance between the magnetometers. A variety of magnetometer types can be used in the magnetometer system, for example, coils or magnets.

In accordance with another embodiment of the invention, a method for monitoring physiological parameters of a subject engaged in a physical activity is provided, the method comprising obtaining a physiology monitoring system including a monitoring garment, a magnetometer subsystem, and a processor subsystem. The monitoring garment is adapted to cover at least a portion of a subject's torso. The magnetometer subsystem has a first magnetometer and a second magnetometer, wherein the first and second magnetometers are responsive to changes in distance therebetween, wherein the magnetometer subsystem is configured to generate and transmit magnetometer signals representing a change in the distance between the first and second magnetometers, wherein the first and second magnetometers are incorporated into the monitoring garment, wherein, when the monitoring garment is worn by the subject, the first and second magnetometers are disposed proximate the subject's chest region. The first and second magnetometers are incorporated into the monitoring garment and are positioned proximate the subject's chest region when the monitoring garment is worn by the subject. The processor subsystem is in communication with the magnetometer subsystem, and programmed and adapted to receive and process the magnetometer signals, and the processor subsystem includes a first empirical relationship for determining movement of the subject's chest wall as a function of the magnetometer signals and a second empirical relationship for determining a respiratory activity of the subject as a function of the chest wall movement. The method further includes positioning the monitoring garment on the subject, acquiring the magnetometer signals with the magnetometers, and determining a chest wall movement with the first empirical relationship and the magnetometer signals.

In accordance with another embodiment, there is provided a monitoring system for noninvasively monitoring physiological parameters of a subject, comprising (i) a wearable monitoring garment adapted to cover at least a portion of a subject's torso, and (ii) a magnetometer system including a first magnetometer and a second magnetometer, the magnetometer system being embedded in the monitoring garment, wherein the first magnetometer is configured to transmit a signal and the second magnetometer is configured to receive a signal from the first magnetometer. One of the first and second magnetometers can be positioned on the front of the subject, preferably in an area corresponding to the subject's chest region. The other of the first and second magnetometers can be positioned on the back of the subject, generally in the same plane as the magnetometer on the subject's chest. The first magnetometer can be adapted to generate a first magnetic field from a first position of the monitoring garment, e.g., the subject's chest area, and the second magnetometer can be adapted to receive the first magnetic field from a second position of the monitoring garment, e.g., the subject's upper back. The magnetometer system is responsive to changes in distance between the first magnetometer and second magnetometer.

In accordance with another embodiment of the invention, there is provided a monitoring system for noninvasively monitoring physiological parameters of a subject, comprising (i) a wearable monitoring garment that is adapted to cover at least a portion of a subject's torso, (ii) a magnetometer subsystem having magnetometers, the magnetometers being responsive to changes in distance therebetween, the magnetometer subsystem being adapted to generate and transmit a plurality of signals, each of the signals representing a change in distance between two or more magnetometers, the magnetometers being embedded in the monitoring garment, a plurality of the magnetometers being embedded in the monitoring garment at a position proximate the subject's chest region, and (iii) a processor subsystem in communication with the magnetometer subsystem and adapted to receive the signals, the processor subsystem being programmed and adapted to control the magnetometer subsystem, the processor subsystem being further programmed and adapted to process the signals, the processor subsystem including at least one empirical relationship for determining at least one respiratory characteristic from the signals, and adapted to generate and transmit at least one respiratory characteristic signal representing the respiratory characteristic.

In some embodiments of the invention, the monitoring system includes a data monitoring subsystem programmed and adapted to receive the respiratory characteristic signal, the data monitoring subsystem being programmed and adapted to recognize and display the respiratory characteristic represented by the respiratory characteristic signal.

In some embodiments of the invention, the monitoring system includes a transmission subsystem adapted to control transmission of the signals from the magnetometer subsystem to the processor subsystem, and the respiratory characteristic signal from the processor subsystem to the data monitoring subsystem.

In some embodiments of the invention, the transmission subsystem includes a wireless communication network.

In some embodiments of the invention, the system includes at least one physiological sensor adapted to detect at least one physiological characteristic associated with the subject, the physiological sensor being further adapted to generate and transmit at least one physiological parameter signal representing the detected physiological characteristic.

In some embodiments of the invention, the system includes at least one spatial parameter sensor adapted to detect orientation and motion of the subject, the spatial parameter sensor being further adapted to generate and transmit a first spatial parameter signal representing a detected orientation of the subject and a second spatial parameter signal representing a detected motion of the subject.

In some embodiments of the invention, at least one of the magnetometer and processor subsystems, and physiological and spatial sensors, is embedded in or carried by the monitoring garment.

In some embodiments of the invention, the processor subsystem is further programmed and adapted to determine movement of the subject's chest wall based on the magnetometer signals, and generate and transmit a chest wall signal representing the chest wall movement.

In some embodiments of the invention, the processor subsystem is further programmed and adapted to determine at least one respiratory activity of the subject based on the chest wall movement, and generate and transmit a respiratory activity signal representing the respiratory activity.

In some embodiments of the invention, the processor subsystem is further programmed and adapted to generate at least one three-dimensional model of the subject's chest wall from the magnetometer signals.

In some embodiments of the invention, the processor subsystem includes a plurality of stored adverse physiological characteristics, and the processor subsystem is further programmed and adapted to compare the detected physiological characteristic to the plurality of stored adverse physiological characteristics, and generate and transmit a warning signal if the detected physiological characteristic is one of the plurality of stored adverse physiological characteristics.

In some embodiments of the invention, the processor subsystem includes a first plurality of chest wall parameters, each of the first plurality of chest wall parameters having at least a plurality of chest wall signals and at least a first spatial parameter associated therewith, each of the first plurality of chest wall parameters representing a first respiratory characteristic and first anatomical parameter.

In some embodiments of the invention, the processor subsystem is further programmed and adapted to compare the magnetometer signals and the spatial parameter signals to the first plurality of chest wall parameters, select a respective one of the first plurality of chest wall parameters based on the magnetometer signals and the spatial parameter signals, and generate and transmit at least a first chest wall parameter signal representing the selected first chest wall parameter.

In accordance with another embodiment of the invention, there is provided a noninvasive method for determining physiological parameters of a subject, comprising the steps of (i) providing a physiology monitoring system, the physiology monitoring system including a magnetometer subsystem and a processor subsystem, the magnetometer subsystem having a plurality of magnetometers, the magnetometers being responsive to changes in distance therebetween, the magnetometer subsystem being adapted to generate and transmit signals, each of the signals representing a change in distance between two or more magnetometers, the processor subsystem being in communication with the magnetometer subsystem, and programmed and adapted to receive and process the signals, the processor subsystem including a first empirical relationship for determining at least one physiological parameter associated with the subject as a function of the signals, (ii) positioning the magnetometers at positions on the subject's body, a plurality of the magnetometers being positioned at a positions proximate the subject's chest region, (iii) acquiring the signals with the first plurality of paired magnetometers, and (iv) determining a first physiological parameter with the first empirical relationship and the signals.

In another embodiment of the invention, the method for determining physiological parameters of a subject comprises (i) providing a physiology monitoring system, the physiology monitoring system including a wearable monitoring garment, a magnetometer subsystem and a processor subsystem, the monitoring garment being adapted to cover at least a portion of a subject's torso, the magnetometer subsystem having magnetometers, the magnetometers being responsive to changes in a spaced distance therebetween, the magnetometer subsystem being adapted to generate and transmit signals, each of signals representing a change in distance between two or more of the magnetometers, the magnetometers being embedded in the monitoring garment, a first plurality of the magnetometers being positioned such that, when the monitoring garment is worn by the subject, the first plurality of magnetometers are disposed proximate the subject's chest region, the processor subsystem being in communication with the magnetometer subsystem, and programmed and adapted to receive and process the signals, the processor subsystem including a first empirical relationship for determining movement of the subject's chest wall as a function of the signals, and a second empirical relationship for determining at least one respiratory activity of the subject as a function of the chest wall movement, (ii) positioning the wearable monitoring garment on the subject, (iii) acquiring the signals with the magnetometers, and (iv) determining a first chest wall movement with the first empirical relationship and the signals.

In one embodiment of the invention, a first respiratory activity of the subject is determined with the second empirical relationship and the first chest wall movement.

In one embodiment, the first chest wall movement is determined with the first empirical relationship and signals generated by the first plurality of paired magnetometers.

BRIEF DESCRIPTION OF THE DRAWINGS/FIGURES

Further features and advantages will become apparent from the following and more particular description of the preferred embodiments of the invention, as illustrated in the accompanying drawings, and in which like referenced characters generally refer to the same parts or elements throughout the views, and in which.

DETAILED DESCRIPTION OF THE INVENTION

Figure 1:
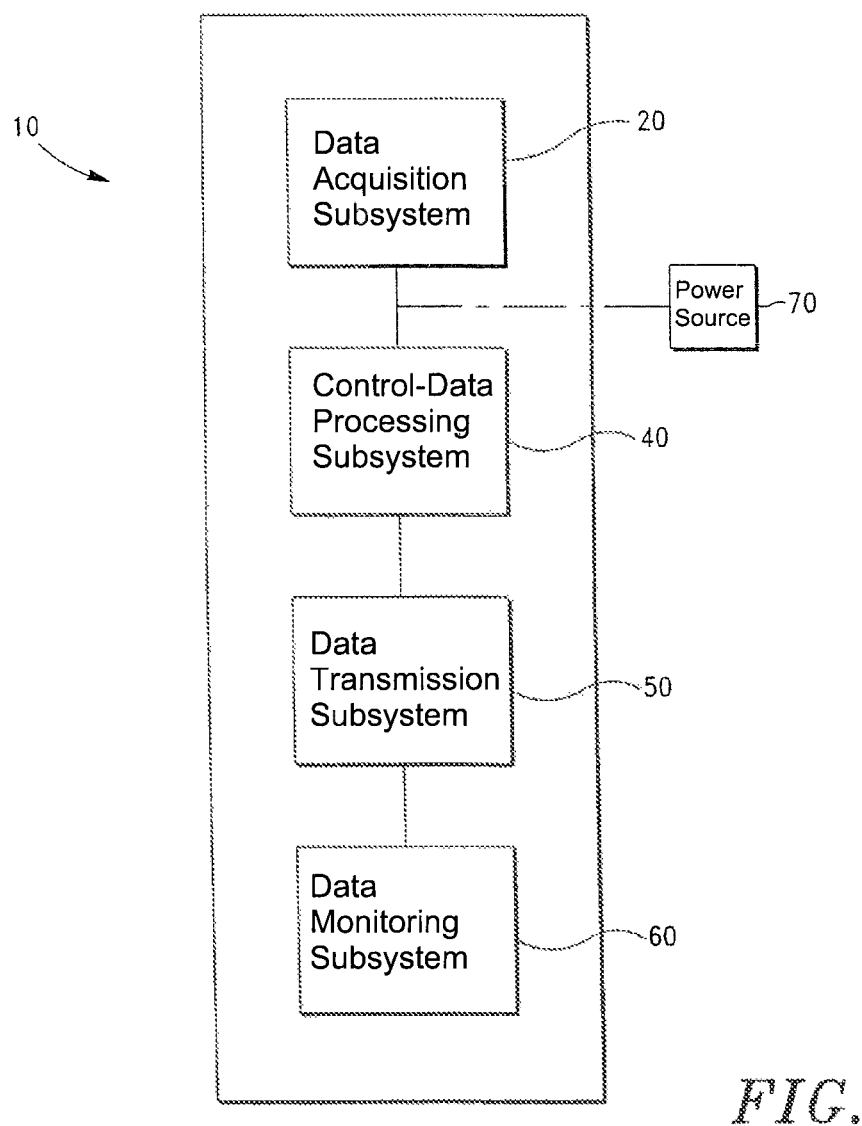
FIG. 1 is a schematic illustration of a physiology monitoring system according to one embodiment of the invention.

Before describing the present invention in detail, it is to be understood that this invention is not limited to particularly exemplified methods, apparatuses, systems, or circuits, as such may, of course, vary. Thus, although a number of methods and systems similar or equivalent to those described herein can be used in the practice of the present invention, the preferred methods, apparatus and systems are described herein.

It is also to be understood that the terminology used herein is for the purpose of describing particular embodiments of the invention only and is not intended to be limiting.

Unless defined otherwise, all technical and scientific terms used herein have the same meaning as commonly understood by one having ordinary skill in the art to which the invention pertains.

As used in this specification and the appended claims, the singular forms "a", "an" and "the" include plural referents unless the content clearly dictates otherwise.

Further, all publications, patents and patent applications cited herein, whether supra or infra, are hereby incorporated by reference in their entirety.

The publications discussed herein are provided solely for their disclosure prior to the filing date of the present application. Nothing herein is to be construed as an admission that the present invention is not entitled to antedate such publication(s) by virtue of prior invention. Further, the dates of publication may be different from the actual publication dates, which may need to be independently confirmed.

Definitions

The terms "respiratory parameter" and "respiratory characteristic", as used herein, mean and include, a characteristic associated with the respiratory system and functioning thereof, including, without limitation, breathing frequency (fB), tidal volume ($V_T$), inspiration volume ($V_1$), expiration volume ($V_E$), minute ventilation ($V_E$), inspiratory breathing time, expiratory breathing time, and flow rates (i.e., rates of change in the chest wall volume). The terms "respiratory parameter" and "respiratory characteristic" further mean and include inferences regarding ventilatory mechanics from synchronous or asynchronous movements of the chest wall compartments.

According to the present invention, flow rates and respiratory accelerations can be determined from a volume signal. Further, numerous inferences regarding ventilatory mechanics can be drawn from the degree of asynchrony in movement occurring amongst the discrete compartments that make up the chest wall.

The terms "respiratory system disorder", "respiratory disorder" and "adverse respiratory event", as used herein, mean and include any dysfunction of the respiratory system that impedes the normal respiration or ventilation process.

The terms "physiological parameter" and "physiological characteristic", as used herein, mean and include, without limitation, electrical activity of the heart, electrical activity of other muscles, electrical activity of the brain, pulse rate, blood pressure, blood oxygen saturation level, skin temperature, and core temperature.

The terms "spatial parameter" and "spatial characteristic", as used herein, mean and include a subject's orientation and/or movement.

The terms "patient" and "subject", as used herein, mean and include humans and animals.

Pulmonary ventilation, tidal volume, respiratory rate, and other associated respiratory characteristics can provide a reliable and practical measure of oxygen and carbon dioxide transpiration in a living body. Respiratory characteristics are directly connected to exercise effort, physiological stress, and other physiological characteristics. One way to externally determine tidal volume is to measure the change in thoracic volume. Change in thoracic volume is caused by the expansion and contraction of the lungs. As the gas pressure in the lungs at the maxima and minima of the pressure ranges is equilibrated to surrounding air pressure, there is a very close and monotonic relationship between the volume of the lungs and the volume of air inspired.

Accurate measurement of the change in thoracic volume involves measuring the change in the diameter of the chest at the ribcage. Measurement of the change in the diameter of the chest below the ribcage can provide additional accuracy to the measurement. Monitoring changes in the diameter of the chest below the ribcage can account for diaphragm delivered breathing where the contraction and relaxation of the diaphragm muscle causes the organs of the abdomen to be pushed down and outwards, thereby increasing the available volume of the lungs.

Monitoring and analyzing respiratory characteristics can be particularly useful in athletic applications, as there is a direct link between performance and an athlete's processing of oxygen and carbon dioxide. For example, in many athletic training situations, it is helpful to know when the athlete's body transitions between aerobic exercise and anaerobic exercise, sometimes referred to as the athlete's ventilatory threshold. Crossing over the ventilatory threshold level is an indicator of pending performance limitations during sport activities. For example, it can be beneficial for athletes to train in the anaerobic state for limited periods of time. However, for many sports, proper training requires only limited periods of anaerobic exercise interrupted by lower intensity aerobic exercises. It is difficult for an athlete to determine which state, anaerobic or aerobic, he or she is in without referencing physiological characteristics such as respiratory characteristics. Therefore, respiratory monitoring and data processing can provide substantial benefits in athletic training by allowing for accurate and substantially instantaneous measurements of the athlete's exercise state. Changes in an athlete's ventilatory threshold over time, as well as patterns of tidal volume during post-exercise recovery, can be valuable to measure improvements in the athlete's fitness level over the course of a training regime. Respiratory monitoring can further allow for monitoring and analyzing changes in a subject's resting metabolic rate.

A second ventilatory threshold exists at the point when the load on the body is such that the pulmonary ventilation is no longer sufficient to support life sustainably. Dwelling too long in this state will lead to collapse and so determination of this point can be of value in medical applications, and particularly to first responders and other emergency response personnel.

As indicated above, the present invention is directed to noninvasive methods and associated systems for monitoring the physiological status of a subject; particularly, the status of the subject's respiratory system. Magnetometers can be used, and can be embedded in or carried by a wearable garment, such as a shirt or vest. The wearable monitoring garment eliminates the need to attach the magnetometers directly to the skin of a subject and, hence, resolves all issues related thereto. The wearable monitoring garment also facilitates repeated and convenient positioning of magnetometers at virtually any appropriate (or desired) position on a subject's torso.

As will be readily appreciated by one having ordinary skill in the art, the methods and systems of the invention provide numerous significant advantages over conventional methods and systems for monitoring physiological status. Among the advantages are the provision of physiology monitoring methods and systems that provide (i) accurate, real-time determination of a plurality of physiological characteristics, (ii) accurate determination of a plurality of respiratory parameters and characteristics, (iii) accurate assessment of chest wall movement(s) and the relationship (s) thereof to respiratory activity and respiratory associated events, such as speaking and coughing, (iv) real-time determination and characterization of respiratory events, and (v) real-time determination and characterization of a subject's orientation and movement.

A further significant advantage is the provision of additional and pertinent data relating to chest wall movement that facilitates three-dimensional modeling of chest wall shape and movement of ambulatory subjects.

Another significant advantage of the present invention is the provision of systems and associated methods that facilitate evaluation and quantification of ventilatory mechanics, e.g, synchronous and asynchronous movement of the chest wall compartments. As will readily be appreciated by one having ordinary skill in the art, this has significant implications in many fields of use, including applications related to specific disease states, such as asthma and chronic obstructive pulmonary disease (COPD), and acute disease states, such as pneumo-thorax and pulmonary embolism.

Another advantage of the present invention is the provision of systems for accurately determining tidal volume ($V_T$) and other respiratory characteristics that do not require complex calibration algorithms and associated methods. This similarly has significant implications in many fields, as well as applications related to many specific disease states, such as COPD.

Several embodiments of the physiology monitoring systems and associated methods of the invention will now be described in detail. It is understood that the invention is not limited to the systems and associated methods described herein. Indeed, as will be appreciated by one having ordinary skill in the art, systems and associated methods similar or equivalent to the described systems and methods can also be employed within the scope of the present invention.

Further, although the physiology monitoring systems and associated methods are described herein in connection with monitoring physiological parameters and characteristics in a human body, the invention is in no way limited to such use. The physiology monitoring systems and associated methods of the invention can also be employed to monitor physiological parameters in non-human bodies. The physiology monitoring systems and associated methods of the invention can also be employed in non-medical contexts, such as determining volumes and/or volume changes in extensible bladders used for containing liquids and/or gasses.

Referring first to FIG. 1, there is shown a schematic illustration of one embodiment of a physiology monitoring system according to the present invention. As illustrated in FIG. 1, the physiology monitoring system 10 preferably includes a data acquisition subsystem 20, a control-data processing subsystem 40, a data transmission subsystem 50, a data monitoring subsystem 60, and a power source 70, such as a battery. Control-data processing subsystem 40 is also referred to herein as "processor subsystem," "processing subsystem," and "data processing subsystem." The terms control-data processing subsystem, processor subsystem, processing subsystem, and data processing subsystem are used interchangeably in the present application.

Data Acquisition Subsystem

In accordance with one embodiment of the invention, the data acquisition subsystem 20 includes means for acquiring anatomical parameters that can be employed to determine at least one respiratory characteristic, more preferably a plurality of respiratory characteristics in cooperation with control-data processing subsystem 40 and, in some embodiments, the data monitoring subsystem 60. The anatomical parameters include changes in (or displacements of) the anteroposterior diameters of the rib cage and abdomen, and axial displacement of the chest wall. The means for acquiring the noted parameters, e.g., sensors. The sensors can comprise paired electromagnetic coils or magnetometers.

Although the present invention is described herein in terms of magnetometers and magnetometer systems, it is understood that other types of sensor systems capable of measuring changes in distance between two or more sensors in the system can be used in place of, or in addition to, magnetometers. Specifically, the invention is not limited to the use of electromagnetic coils or magnetometers to measure changes in the anteroposterior diameters of the rib cage and abdomen, and axial displacement of the chest wall. Various additional means and devices that can be readily adapted to measure the noted anatomical parameters can be employed within the scope of the invention. Such means and devices include, without limitation, Hall effect sensors and electronic compass sensors. Wireless sensors with the capability of measuring time delay in a signal sent from one sensor to another and thereby determine the distance between the two sensors can be substituted for or provided in addition to magnetometers in accordance with the present invention.

According to the invention, at least one, and preferably two, magnetometers can be employed to measure the noted subject parameters (or displacements). In some embodiments of the invention, two pairs of magnetometers are thus employed. In some embodiments, more than two pairs of magnetometers are employed.

Figure 2:
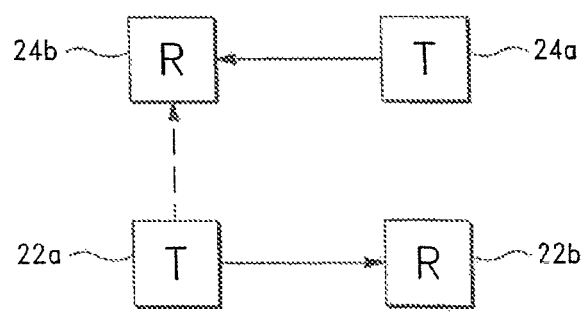
FIG. 2 is a schematic illustration of a dual-paired electromagnetic coil arrangement, according to one embodiment of the invention.

Referring now to FIG. 2, there is shown one embodiment of a dual-paired electromagnetic coil arrangement for detecting and measuring displacement(s) of the rib cage, abdomen, and chest wall. As illustrated in FIG. 2, the electromagnetic coils include first transmission and receive coils 22a and 22b and second transmission and receive coils 24a and 24b. In FIG. 2, the letter T designates the transmission coils and the letter R designates the receiving coils. In FIG. 2, the letter T designates the transmission coils and the letter R designates the receiving coils, however, the coils are not limited to such designations. The electromagnetic coils of embodiments of the present invention are described as "receiving" or "transmitting," however, each receiving coil can alternatively and independently be a transmitting coil, and each transmitting coil can alternatively and independently be a transmitting coil. Coils can also perform both receiving and transmitting functions.

Details of the noted arrangement and associated embodiments (discussed below) are set forth in U.S. patent application Ser. No. 12/231,692, filed Sep. 5, 2008, co-pending U.S. Patent Application No. 61/275,576, filed Sep. 1, 2009, and co-pending U.S. patent application Ser. No. 12/869,576, filed concurrently herewith, each of which, as indicated above, is expressly incorporated by reference herein in its entirety.

As set forth in the noted applications, in some embodiments of the invention, at least receive coil 24b is adapted to receive coil transmissions from each of transmission coils 22a, 24a (i.e., at least receive coil 24b may be a dual function coil, where "dual function coil" refers to a coil capable of receiving transmissions from a plurality of different transmission coils). In some embodiments, each receive coil 22b, 24b is adapted to receive transmissions from each transmission coil 22a, 24a.

Figure 3:
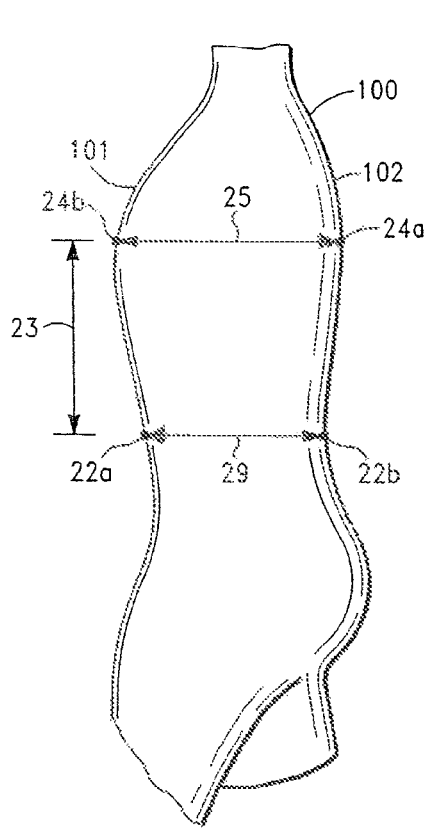
FIG. 3 is a side view of a subject, showing the position of the dual-paired electromagnetic coil arrangement shown in FIG. 2 on the subject, according to one embodiment of the invention.
Figure 4:
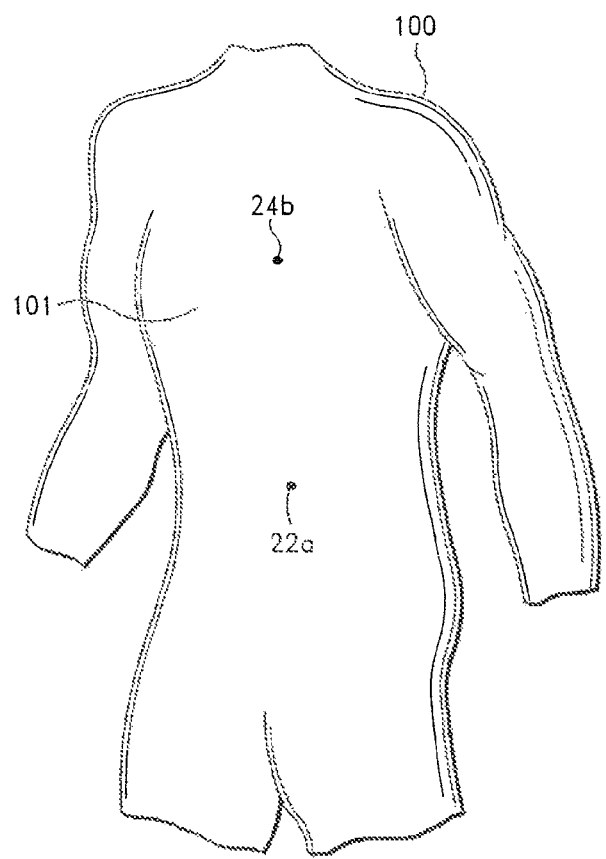
FIG. 4 is a perspective view of the subject, showing the position of electromagnetic coils on the front of the subject, according to one embodiment of the invention.
Figure 5:
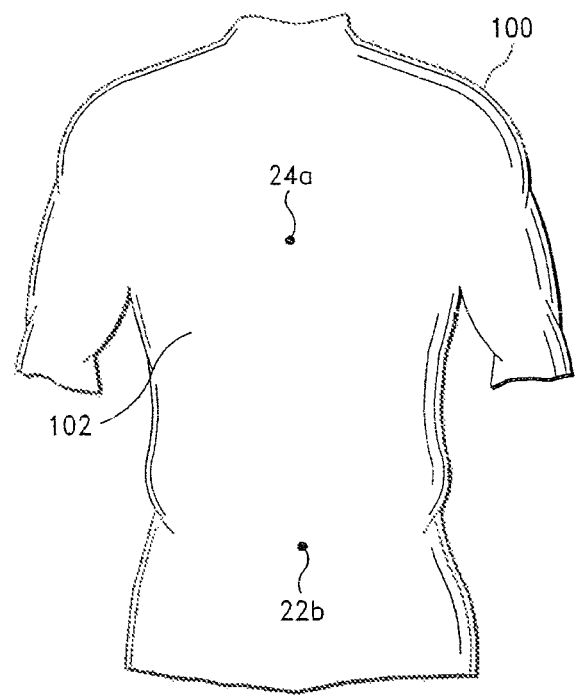
FIG. 5 is a plane view of the subject's back, showing the position of electromagnetic coils thereon, according to one embodiment of the invention.

Referring now to FIGS. 3-5, there is shown the position of coils 22a, 22b, 24a, 24b on a subject or patient 100, in accordance with one embodiment of the invention. As illustrated in FIGS. 3-5, first transmission coil 22a is preferably positioned on front 101 of subject 100 proximate the umbilicus of subject 100, and first receive coil 22b is preferably positioned proximate the same axial position, but on back 102 of subject 100. Second receive coil 24b is preferably positioned on front 101 of subject 100 proximate the base of the sternum, and second transmission coil 24a is preferably positioned proximate the same axial position, but on back 102 of subject 100.

As set forth in co-pending U.S. patent application Ser. No. 12/231,692, the positions of transmission coils 22a, 24a and receive coils 22b, 24b can be reversed (i.e., transmission coil 22a and receive coil 24b can be placed on back 102 of subject 100 and transmission coil 24a and receive coil 22b can be placed on front 101 of subject 100. Both transmission coils 22a and 24a can also be placed on front 101 or back 102 of subject 100 and receive coils 22b and 24b can be placed on the opposite side.

Referring back to FIG. 3, an arrow 23 represents the chest wall or, in this instance, the xiphi-umbilical distance (Xi) that is monitored. An arrow 25 represents the monitored rib cage distance, while an arrow 29 represents the monitored abdominal distance.

In accordance with one embodiment of the invention, wherein coil 24b is a dual function coil, as subject or patient 100 breathes, displacement(s) of the rib cage and abdomen (i.e., changes in the distance between each pair of coils 22a, 22b and 24a, 24b, denoted, respectively, by arrow 29 and arrow 25), is determined from measured changes in voltage between paired coils 22a, 22b and 24a, 24b. The axial displacement of the chest wall, denoted by arrow 23, (e.g., xiphi-umbilical distance (Xi)), is also determined from measured changes in voltage between transmission coil 22a and receive coil 24b.

As indicated above, in some embodiments of the invention, more than two pairs of electromagnetic coils can be employed. As set forth in co-pending U.S. Patent Application No. 61/275,575, filed Sep. 1, 2009, and co-pending U.S. patent application Ser. No. 12/869,585, filed concurrently herewith, each of which is incorporated by reference herein in its entirety, adding additional electromagnetic coils in anatomically appropriate positions on a subject provides numerous significant advantages over dual-paired coil embodiments. Among the advantages is the provision of additional (and pertinent) data and/or information regarding chest wall movement(s) and the relationship(s) thereof to respiratory activity and respiratory associated events, such as speaking, sneezing, laughing, and coughing.

Further, the multiple single, cross and interaction axes of the electromagnetic coil transmissions that result from the additional coils (and placement thereof) provide highly accurate quantification of changes in chest wall volume, and facilitate three-dimensional modeling of chest wall shape and movement of ambulatory subjects, and the evaluation and quantification of ventilatory mechanics, e.g., synchronous and asynchronous movement of the chest wall compartments.

Referring now to FIGS. 6-17, the multiple-paired coil embodiments of the invention will now be described in detail. It is, however, to be understood that the invention is not limited to the multiple-paired coil embodiments described herein. Indeed, the multiple-paired coil embodiments can comprise any number of additional electromagnetic coils, e.g., 3, 4, 5, 6, 7, 8, etc. For example, in embodiments using three magnetometers, for example, electromagnetic coils, it is understood that the three electromagnetic coils can function as multiple pairs. Specifically, referring to the coils as first, second, and third coils, the first coil can form a pair with the second coil and the first coil can also form a pair with the third coil. In addition, the second coil can also form a pair with the third coil. Thus, a magnetometer system utilizing three electromagnetic coils can be configured to form one, two, or three pairs. Each of the first, second, and third coils can be configured to transmit signals, receive signals, or to both receive and transmit signals. A magnetometer can communicate with a plurality of other magnetometers, and therefore a particular magnetometer can form a part of more than one pair. The position of the additional coils and the function thereof can also be readily modified and/or adapted for a particular application within the scope of the present invention.

Figure 6:
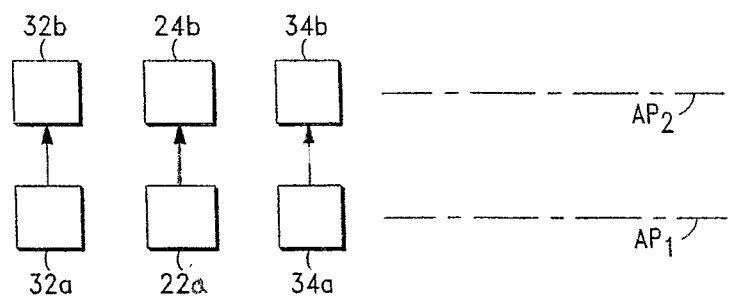
FIGS. 6 and 7 are schematic illustrations of a multiple-paired electromagnetic coil arrangement, according to one embodiment of the invention.
Figure 7:
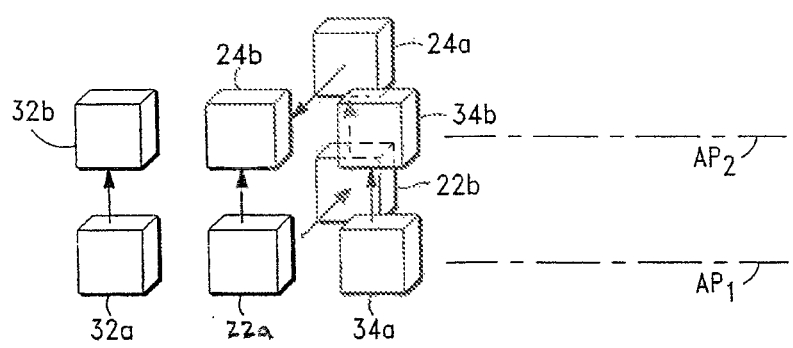
Figure 8:
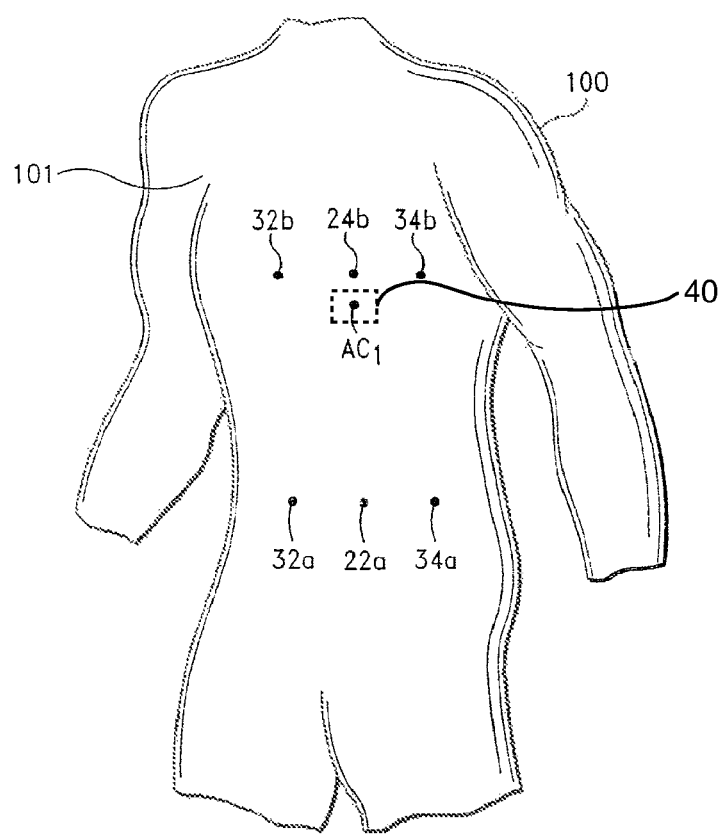
FIG. 8 is a perspective view of a subject, showing the position of the multiple-paired electromagnetic coils shown in FIG. 6 on the front of the subject, according to one embodiment of the invention.

Referring first to FIGS. 6-8, there is shown one embodiment of the multiple-paired coil embodiment of the invention. As illustrated in FIG. 7, the noted embodiment similarly includes electromagnetic coils 22a, 22b, 24a, 24b. According to the invention, any of the aforementioned dual-paired coil embodiments associated with coils 22a, 22b, 24a, 24b can be employed with the multiple-paired coil embodiments of the invention.

As also illustrated in FIGS. 6 and 7, the multiple-paired coil embodiment can further includes at least two additional pairs of electromagnetic coils: third transmission coil 32a, third receive coil 32b, fourth transmission coil 34a, and fourth receive coil 34b.

In some embodiments of the invention, at least one of the two additional receive coils 32b, 34b is a dual function coil and, hence, adapted to receive transmissions from each of transmission coils 32a, 22a, 34a. In some embodiments, each receive coil 32b, 34b is adapted to receive transmissions from each transmission coil 32a, 22a, 34a.

Figure 9:
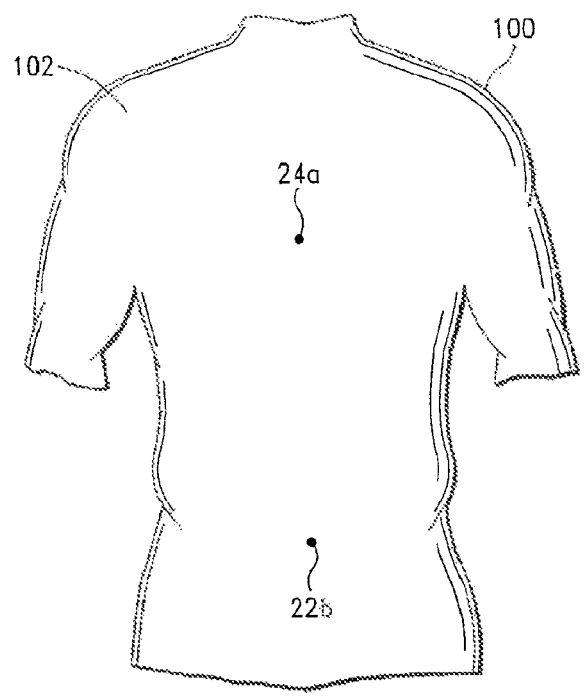
FIG. 9 is a plane view of the subject's back, showing the position of electromagnetic coils thereon, according to one embodiment of the invention.

Referring now to FIGS. 8 and 9, there is shown the position of coils 22a, 22b, 24a, 24b, 32a, 32b, 34a, 34b on a subject or patient 100, in accordance with one embodiment of the invention. As illustrated in FIGS. 8 and 9, first transmission coil 22a is preferably positioned on front 101 of subject 100 proximate the umbilicus of subject 100, and first receive coil 22b is preferably positioned proximate the same axial position, but on back 102 of subject 100. Second receive coil 24b is preferably positioned on front 101 of subject 100 proximate the base of the sternum, and second transmission coil 24a is positioned proximate the same axial position, but on back 102 of subject 100.

Third transmission coil 32a is preferably positioned on front 101 of subject 100 and axially spaced to the right of first transmission coil 22a. Fourth transmission coil 34a is preferably positioned on front 101 of subject 100 and axially spaced to the left of first transmission coil 22a. In the illustrated embodiment, each transmission coil 32a, 22a, 34a is preferably positioned proximate the same axial plane (denoted "$AP_1$" in FIGS. 6 and 7).

Third receive coil 32b is preferably positioned on front 101 of subject 100 and axially spaced to the right of second receive coil 24b. Fourth receive coil 34b is preferably positioned on front 101 of subject 100 and axially spaced to the left of second receive coil 24b. Preferably, each receive coil 32b, 24b, 34b is similarly positioned proximate the same axial plane (denoted "$AP_2$" in FIGS. 6 and 7).

The third receive coil 32b is also preferably positioned on the front 101 of the subject 100 and axially spaced to the right of second receive coil 24b. The fourth receive coil 34b is also preferably positioned on the front 101 of the subject 100 and axially spaced to the left of second receive coil 24b. Preferably, each receive coil 34, 28, 38 is similarly positioned proximate the same axial plane (denoted "$AP_2$" in FIGS. 6 and 7).

As will readily be appreciated by one having ordinary skill in the art, the axial spacing of coils 32a, 32b, 34a, 34b will, in many instances, be dependant on the body size and structure of the subject, e.g., adult, female, male, adolescent, etc. The distance between and amongst the coils can also vary with the degree of measurement precision required or desired.

Preferably, in the noted embodiment, the axial spacing between coils 32a, 32b, 34a, 34b and coils 22a, 22b, 24a, 24b is substantially equal or uniform.

As indicated above, a significant advantage of the multiple-paired coil embodiments of the invention is the provision of multiple single, cross and interaction coil transmission axes that facilitate three-dimensional modeling of chest wall shape and movement of ambulatory subjects, and evaluation and quantification of ventilatory mechanics, e.g., synchronous and asynchronous movement of the chest wall compartments.

A further significant advantage of the multiple-paired coil embodiments of the invention is that real-time, three-dimensional models of the chest wall can be created by simultaneous monitoring of the chest wall with the multiple-paired coils of the invention.

Another advantage is that with sufficiently tight tolerances on the coil field strength(s), volume calibration would not be necessary. Measurement precision would, thus, be determined by the geometrical void spaces between the various coil pairs.

Figure 10:
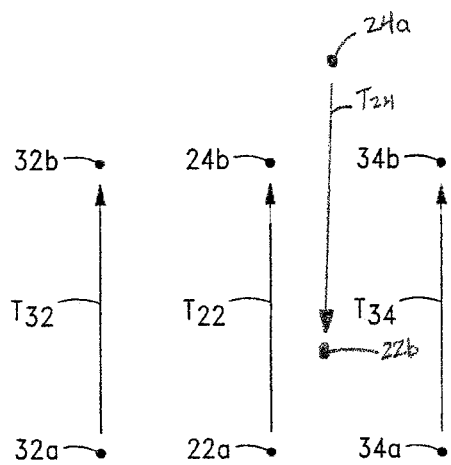
FIGS. 10-12 are schematic illustrations of coil transmission axes provided by several multiple-paired coil embodiments of the invention.
Figure 11:
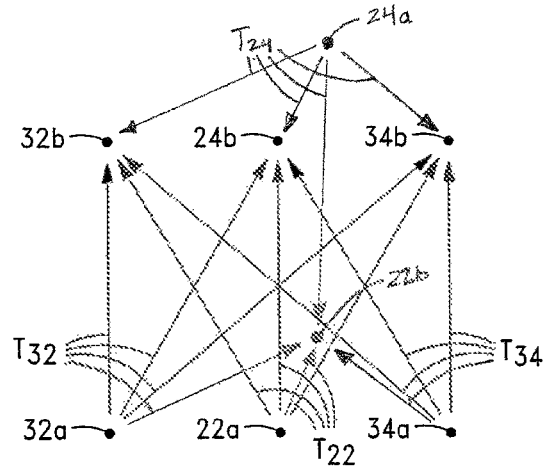
Figure 12:
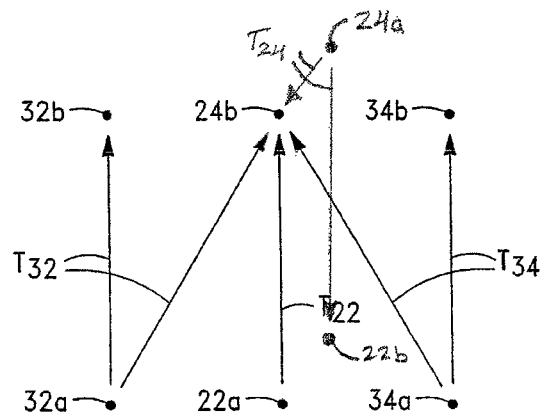

Referring now to FIGS. 10-12, there are shown several schematic illustrations of coil transmission axes provided by three multiple-paired coil embodiments of the invention. Referring first to FIG. 10, there is shown one embodiment, wherein each receive coil 32b, 24b, 34b, 22b is a single function coil. Receive coil 32b is adapted to receive a transmission $T_{32}$ from transmission coil 32a. Receive coil 24b is adapted to receive a transmission $T_{22}$ from transmission coil 22a. Receive coil 34b is adapted to receive a transmission $T_{34}$ from transmission coil 34a. Receive coil 22b is adapted to receive a transmission $T_{24}$ from transmission coil 24a.

Referring now to FIG. 12, there is shown another embodiment, wherein receive coil 24b is a dual function coil. Receive coil 32b is adapted to receive transmission $T_{32}$ from transmission coil 32a, receive coil 34b is adapted to receive transmission $T_{34}$ from transmission coil 34a, and receive coil 22b is adapted to receive transmission $T_{24}$ from transmission coil 24a. Receive coil 24b is, however, adapted to receive transmission $T_{32}$ from transmission coil 32a, transmission $T_{22}$ from transmission coil 22a, transmission $T_{34}$ from transmission coil 34a, and transmission $T_{24}$ from transmission coil 24a.

In a further embodiment, illustrated in FIG. 11, each receive coil 32b, 24b, 34b, 22b is a dual function coil. As illustrated in FIG. 11, receive coil 32b is adapted to receive transmission $T_{32}$ from transmission coil 32a, transmission $T_{22}$ from transmission coil 22a, transmission $T_{34}$ from transmission coil 34a, and transmission $T_{24}$ from transmission coil 24a. Receive coils 24b, 34b, and 22b are also adapted to receive transmission $T_{32}$ from transmission coil 32a, transmission $T_{22}$ from transmission coil 22a, transmission $T_{34}$ from transmission coil 34a, and transmission $T_{24}$ from transmission coil 24a.

The noted multiple-paired coil embodiments thus significantly enhance the available data and information associated with chest wall movement and, hence, respiratory activity and respiratory associated events. The additional data and information also facilitates the evaluation and quantification of ventilatory mechanics, e.g., synchronous and asynchronous movement of the chest wall compartments.

The supplemental coil transmissions (or signals) can also be readily employed to reduce or eliminate the frequency and impact of magnetic field interference and artifacts, which are commonly encountered in electromagnetic coil systems.

As indicated above, the multiple-paired coil embodiments of the invention are not limited to the embodiment described above, wherein two additional pairs of electromagnetic coils are uniformly positioned on the front of a subject. Referring now to FIGS. 13-17, there are shown additional multiple-paired coil embodiments of the invention.

Figure 13:
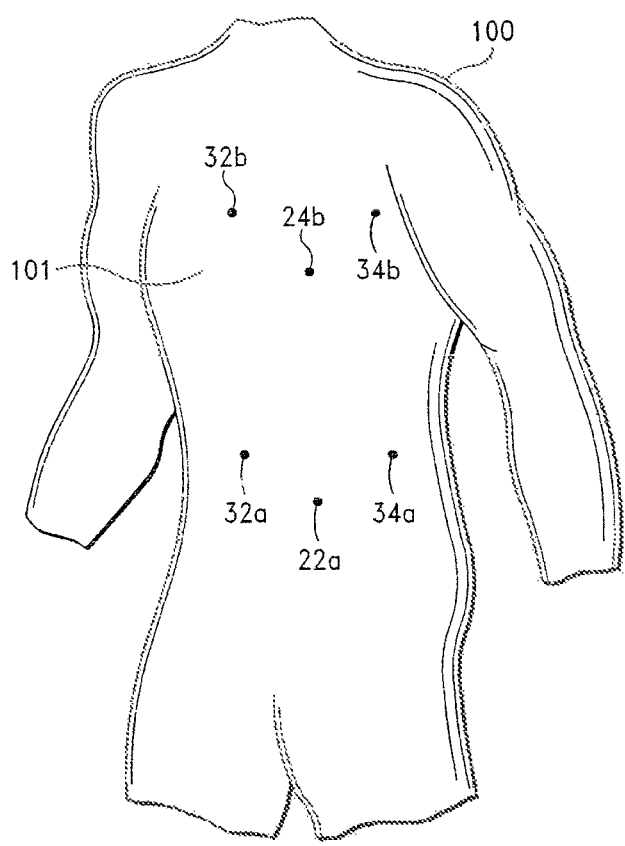
FIG. 13 is a perspective view of a subject, showing alternative positions of the multiple-paired electromagnetic coils shown in FIG. 6 on the front of the subject, according to another embodiment of the invention.

Referring first to FIG. 13, there is shown a multiple-paired coil embodiment, wherein the two additional coil pairs 32a, 32b, and 34a, 34b are non-uniformly positioned on front 101 of subject 100. As indicated, the additional coil pairs can be positioned at any appropriate (or desired) positions on the torso of subject 100.

Figure 14:
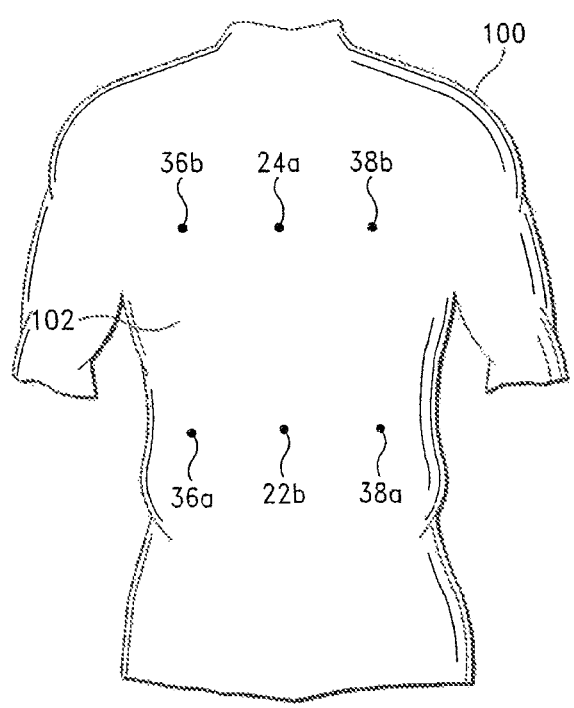
FIG. 14 is a plane view of the subject's back, showing the positioning of three pairs of electromagnetic coils thereon, according to another embodiment of the invention.
Figure 15:
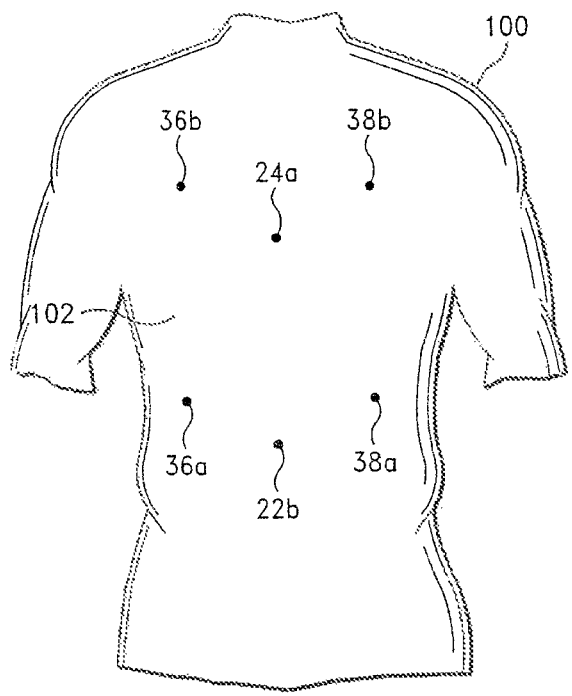
FIG. 15 is a plane view of the subject's back, showing alternative positions of the paired electromagnetic coils shown in FIG. 14 thereon, according to another embodiment of the invention.

Additional paired coils (e.g., transmission coil 36a paired with receive coil 36b, and transmission coil 38a paired with receive coil 38b) can also be positioned on back 102 of subject 100, as illustrated in FIG. 14. Coils 36a, 36b, 38a, 38b can be positioned uniformly, as shown in FIG. 14, or non-uniformly, as illustrated in FIG. 15.

Figure 16:
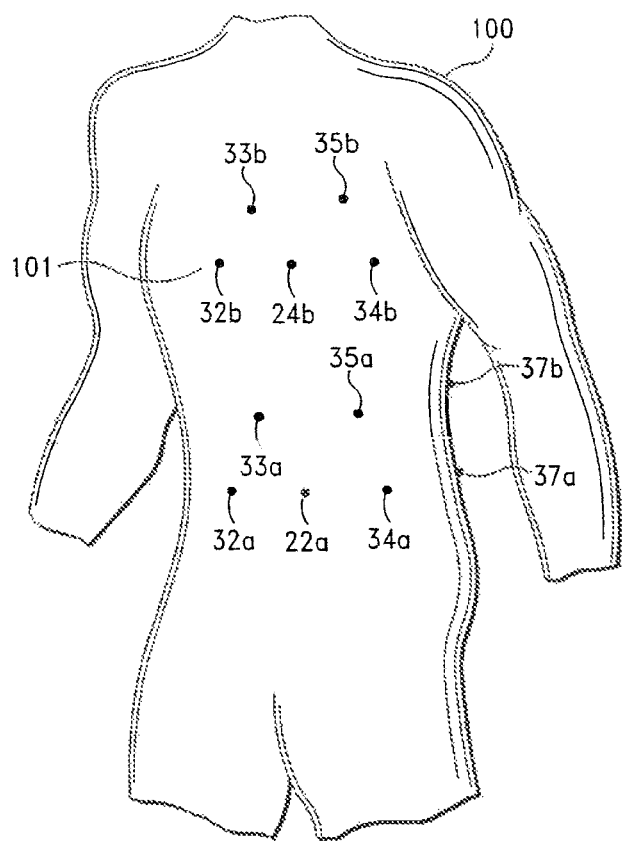
FIG. 16 is a perspective view of a subject, showing the position of six pairs of electromagnetic coils on the front and one side of the subject, according to another embodiment of the invention.
Figure 17:
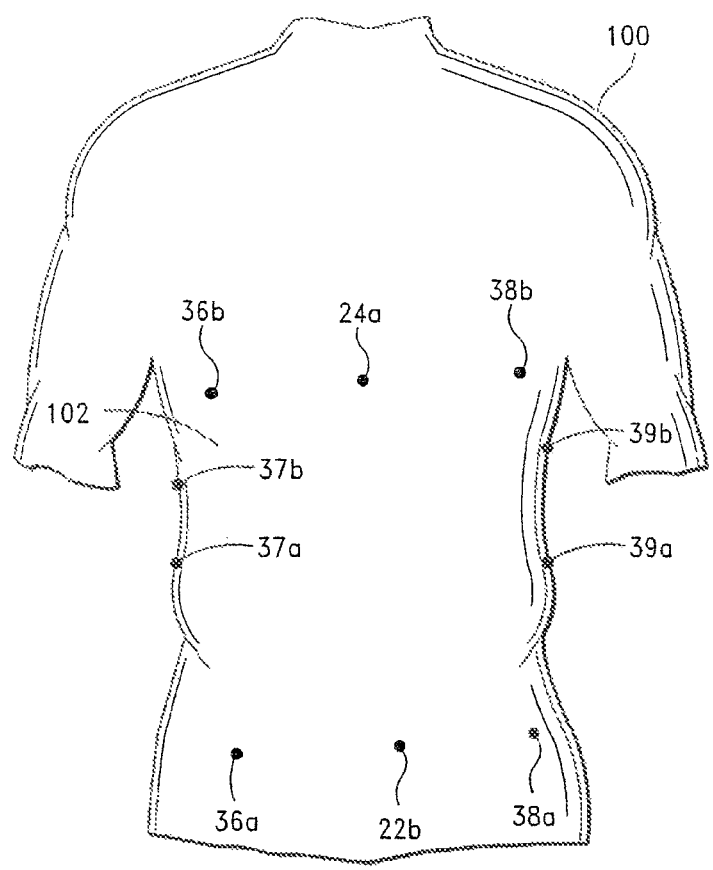
FIG. 17 is a plane view of the subject's back, showing the position of five pairs of electromagnetic coils on the back and both sides of the subject, according to another embodiment of the invention.

Referring now to FIGS. 16-17, there is shown another multiple-paired coil embodiment, wherein additional paired coils are positioned on the torso of subject 100. As illustrated in FIG. 16, additional paired coils (e.g., transmission coil 33a paired with receive coil 33b, and transmission coil 35a paired with receive coil 35b) can be positioned on front 101 of subject 100. In the noted embodiment, transmission coil 33a is preferably positioned above and between transmission coils 32a and 22a, and transmission coil 35a is preferably positioned above and between transmission coils 22a and 34a. Receive coil 33b is preferably positioned above and between receive coils 32b and 24b, and receive coil 35b is preferably positioned above and between receive coils 24b and 34b.

As illustrated in FIGS. 16 and 17, additional paired coils (e.g., transmission coil 37a paired with receive coil 37b, and transmission coil 39a paired with receive coil 39b) can be also positioned on opposite sides of the subject 100.

Additionally, the transmission coils and receive coils disclosed herein need not necessarily be paired one-to-one. For example, a single receive coil may be configured to receive transmissions from multiple transmission coils, and a single transmission coil may be configured to transmit to multiple receive coils.

As indicated above, the multiple-paired coil embodiments of the invention are not limited to the multiple-paired coil embodiments shown in FIGS. 6-17. It is again emphasized that the multiple-paired coil embodiments can include any number of additional pairs of electromagnetic coils. Further, the position of the additional coils and the function thereof can also be readily modified and/or adapted for a particular application within the scope of the present invention.

In some embodiments of the invention, the data acquisition subsystem 20 can include means for directly monitoring the subject's orientation and/or movement, e.g., spatial parameters. According to the invention, various conventional means can be employed to monitor or measure subject orientation and movement, including optical encoders, proximity and Hall effect switches, laser interferometry, accelerometers, gyroscopes, and/or global positioning systems (GPS).

In one embodiment, the means for directly monitoring the orientation and movement of a subject includes at least one multi-function inertial sensor (e.g., 3-axis accelerometer or 3-axis gyroscope). As is well known in the art, orientation and motion of a subject can be readily determined from the signals or data transmitted by a multi-function inertial sensor.

According to the invention, the accelerometer can be disposed in any anatomically appropriate position on a subject. In one embodiment of the invention, an accelerometer (denoted "$AC_1$" in FIG. 8) is disposed proximate the base of the subject's sternum.

Control-Data Processing Subsystem

According to the present invention, control-data processing subsystem 40 can include programs, instructions, and associated algorithms for performing the methods of the invention, including control algorithms and associated parameters to control data acquisition subsystem 20 and, hence, the paired electromagnetic coils, e.g., coils 22a, 22b, 24a, 24b, 32a, 32b, 34a, 34b and the function thereof, and the transmission and receipt of coil transmissions, e.g., transmissions $T_{32}$, $T_{22}$, $T_{34}$, and $T_{24}$, as well as data transmission subsystem 50 and data monitoring subsystem 60. Such is discussed in detail below.

Control-data processing subsystem 40 is further programmed and adapted to retrieve and process coil transmissions or signals from the electromagnetic coils (e.g., coils 22a, 22b, 24a, 24b, 32a, 32b, 34a, 34b) in order to determine physiological information associated with monitored subject 100, to retrieve, process, and interpret additional signals transmitted by additional spatial parameter and physiological sensors (discussed below), and to transmit selective coil data, physiological and spatial parameters, physiological characteristics, and subject information to data monitoring subsystem 60.

In a preferred embodiment of the invention, control-data processing subsystem 40 further includes at least one "n-degrees-of-freedom" model or algorithm for determining at least one respiratory characteristic (e.g., $V_T$) from the retrieved coil transmissions or signals (e.g., measured displacements of the rib cage, abdomen, and chest wall).

In one embodiment, control-data processing subsystem 40 includes one or more "three-degrees-of-freedom" models or algorithms for determining at least one respiratory characteristic (preferably, a plurality of respiratory characteristics) from the retrieved coil transmissions (or signals). Preferred "three-degrees-of-freedom" models (or algorithms) are set forth in co-pending U.S. patent application Ser. No. 12/231,692.

In some embodiments, control-data processing subsystem 40 is further programmed and adapted to assess physiological characteristics and parameters by comparison with stored physiological benchmarks. Control-data processing subsystem 40 can also be programmed and adapted to assess respiratory and spatial characteristics and parameters by comparison with stored respiratory and spatial benchmarks Control-data processing subsystem 40 can generate status signals if corresponding characteristics or parameters are present. The benchmarks may indicate, for example, adverse conditions or fitness goals, and the status signals may include warnings or alarms.

Control-data processing subsystem 40 also preferably includes suitable algorithms that are designed and adapted to determine respiratory characteristics, parameters and status from measured multiple, interactive chest wall displacements. The algorithms are also preferably adapted to subtract measured chest wall displacements that are associated with non-respiration movement, e.g., twisting of the torso, to enhance the accuracy of respiratory characteristic (and/or parameter) determinations.

The control-data processing subsystem 40 additionally preferably includes suitable programs, algorithms and instructions to generate three-dimensional models of a subject's chest wall from the measured multiple, interactive chest wall displacements.

According to the invention, various programs and methods (e.g., differential geometric methods) can be employed to process the signals (reflecting the chest wall distances and displacement) into a representation of the shape of the torso. Indeed, it is known that providing sufficient distances defined on a two dimensional surface (a metric) permit the shape of the surface to be constructed in a three dimensional space. See, e.g., Badler, et al., "*Simulating Humans: Computer Graphics, Animation, and Control*", (New York: Oxford University Press, 1993) and DeCarlo, et al., "*Integrating Anatomy and Physiology for Behavior Modeling*", Medicine Meets Virtual Reality 3 (San Diego, 1995).

Preferably, in some embodiments of the invention, the control-data processing subsystem 40 is further programmed and adapted to determine additional and, in some instances, interrelated anatomical parameters, such as bending, twisting, coughing, etc., from the measured multiple, interactive chest wall displacements. In one embodiment, the control-data processing subsystem 40 is programmed and adapted to compare retrieved coil transmissions reflecting measured chest wall displacements with stored selective combinations of coil transmissions and chest wall parameters that are associated therewith, e.g., "normal respiration and bending", "normal respiration and coughing", etc.

By way of example, in one embodiment, a first chest wall parameter ($CWP_1$) defined as (or reflecting) "normal respiration and twisting of the torso" is stored in the control-data processing subsystem 40. The coil transmissions and data associated with the first chest wall parameter ($CWP_1$) include transmissions $T_{32}$, $T_{22}$, $T_{34}$, and $T_{24}$ received by receive coil 24b that can represent displacements x, y, and z.

During monitoring of subject 100, similar coil transmissions may be received by receive coil 24b. Control-data processing system 40 then compares the detected (or retrieved) transmissions to the stored transmissions and chest wall parameter associated therewith to determine (in real-time) the chest wall movement and, hence, respiratory activity based thereon; in this instance "normal respiration and twisting of the torso".

In some embodiments, the signals transmitted by the accelerometer (e.g, spatial parameter signals) are employed with the detected coil transmissions to determine and classify chest wall movement and associated respiratory activity of the monitored subject. In the noted embodiments, each stored chest wall parameter also includes spatial parameter signals associated with the chest wall parameter, e.g., normal respiration and twisting of the torso. According to the invention, the control-data processing system 40 is adapted to compare retrieved coil transmissions and spatial parameter signals to the stored transmissions and spatial parameter signals, and the chest wall parameters associated therewith, to determine the chest wall movement and, hence, respiratory activity based thereon.

In some embodiments, the spatial parameter signals are used to generate a spatial model of the subject. The spatial model can be two-dimensional or three-dimensional, and can reflect the real-time orientation and movement of the subject. The spatial model can be displayed to provide the subject or another with a representation of the real-time orientation and movement of the subject.

In some embodiments of the invention, the control-data processing system 40 is programmed and adapted to determine chest wall movement and respiratory activity based on retrieved coil transmissions, spatial parameter signal and audio signals. In the noted embodiments, the data acquisition subsystem 20 can also include an audio sensor, e.g., a microphone, that is disposed in an anatomically appropriate position on a subject, e.g., proximate the throat.

According to the invention, each stored chest wall parameter also includes at least one audio parameter, e.g. >N db (based on the audio signal) that is associated with the chest wall parameter, e.g., normal respiration and coughing. Suitable speech and cough parameters (and threshold determinations) are set forth in U.S. Pat. No. 7,267,652, issued Sep. 11, 2007, which is incorporated by reference herein in its entirety.

Upon receipt of coil transmissions, spatial parameter signals and audio signal, the control-data processing system 40 compares the retrieved coil transmissions, spatial parameter signals, and audio signals to the stored transmissions, spatial parameter signals and audio parameters, and the chest wall parameter associated therewith, to determine the chest wall movement and respiratory activity based thereon, e.g., normal respiration and coughing.

In some embodiments of the invention, control-data processing system 40 is programmed and adapted to determine fitness activity based on retrieved coil transmissions, spatial parameter signals, and audio signals. In the noted embodiments, data acquisition subsystem 20 may also include an audio sensor, such as, for example, a microphone, that is disposed in an anatomically appropriate position on a subject (e.g., proximate the throat).

Upon receipt of coil transmissions, spatial parameter signals, and audio signals, control-data processing system 40 compares the retrieved coil transmissions, spatial parameter signals, and audio signals to the stored transmissions, spatial parameter signals, and audio parameters, and the chest wall parameters associated therewith, to determine a fitness activity of the subject (e.g., running, jogging, stretching, swimming, performing push-ups, performing sit-ups, performing chin-ups, performing arm curls, playing basketball, playing baseball, or playing soccer).

Data Monitoring Subsystem

According to embodiments of the invention, data monitoring subsystem 60 is designed and adapted to receive and, in some embodiments, to selectively monitor coil transmissions or signals (e.g., transmissions $T_{32}$, $T_{22}$, $T_{34}$, and $T_{24}$) and to display parameters associated therewith (e.g., displacement(s) along a selective axis), and/or a chest wall parameter (e.g., $CWP_1$), and/or a respiratory characteristic (e.g., $V_T$) or event.

Data monitoring subsystem 60 is further preferably designed and adapted to display selective subject parameters, characteristics, information, and warnings or alarms. Data monitoring subsystem 60 can also be adapted to display data or broadcast data aurally. The aurally presented data can be voice messages, music, or other noises signifying an event. Data monitoring subsystem 60 can be adapted to allow headphones or speakers to connect to the data monitoring subsystem, either wireless or wired, to broadcast the aural data. Data monitoring subsystem 60 can be adapted to include a display, or to allow a display to connect to the data monitoring subsystem, to display the data. Such display can include, for example, a liquid crystal display (LCD), a plasma display, a cathode ray tube (CRT) display, a light emitting diode (LED) display, or an organic light emitting diode (OLED) display.

In some embodiments of the invention, data monitoring subsystem 60 is also adapted to receive and, in some embodiments, selectively monitor spatial parameter signals and signals transmitted by additional anatomical and physiological sensors (e.g., signals indicating skin temperature, or $SpO_2$) and to display parameters and information associated therewith. The parameters can be associated with an athlete's physical activity. Physical or anatomical parameters measured and/or calculated may include, for example, time, location, distance, speed, pace, stride count, stride length, stride rate, and/or elevation. Physiological parameters measured and/or calculated may include, for example, heart rate, respiration rate, blood oxygen level, blood flow, hydration status, calories burned, muscle fatigue, and/or body temperature. In an embodiment, performance parameters may also include mental or emotional parameters such as, for example, stress level or motivation level. Mental and emotional parameters may be measured and/or calculated directly or indirectly either through posing questions to the athlete or by measuring things such as, for example, trunk angle or foot strike characteristics while running.

In some embodiments of the invention, the data monitoring subsystem 60 comprises a local electronic module or local data unit (LDU). By the term "local" as used in connection with a LDU, it is meant that the LDU is disposed close to the electromagnetic coils, such as on or in a wearable garment containing the coils (which is discussed in detail below).

In some embodiments of the invention, the LDU is preferably adapted to receive and monitor coil transmissions (or signals), preprocess the coil transmissions, store the coil transmissions and related data, and display selective data, parameters, physiological characteristics and subject information.

In some embodiments, the LDU is also adapted to receive and monitor the spatial parameter transmissions (or signals) and additional signals transmitted by additional anatomical and physiological sensors (if employed), and preprocess the signals, store the signals and related data, and display selective data, physiological and spatial parameters, physiological characteristics and subject information via a variety of media, such as a personal digital assistant (PDA), a mobile phone, and/or a computer monitor, etc.

In some embodiments, the LDU includes a remote monitor or monitoring facility. In these embodiments, the LDU is further adapted to transmit selective coil and sensor data, physiological parameters and characteristics, spatial parameters, and subject information to the remote monitor or facility.

In some embodiments of the invention, the LDU includes the features and functions of the control-data processing subsystem 40 (e.g, an integral control-processing/monitoring subsystem) and, hence, is also adapted to control the data acquisition subsystem 20. The LDU is thus adapted to control the paired coils that are employed, determine selective physiological characteristics and parameters, and assess physiological characteristics and parameters for adverse conditions, and generate warnings or alarms if adverse characteristics or parameters are present.

Suitable LDUs are described in co-pending International Application No. PCT/US2005/021433 (Pub. No. WO 2006/009830 A2), published Jan. 26, 2006, which is incorporated by reference herein in its entirety.

In some embodiments of the invention, the monitoring subsystem 60 comprises a separate, remote monitor or monitoring facility. According to the invention, the remote monitor or facility is adapted to receive sensor data and information, physiological and spatial parameters, physiological characteristics and subject information from the control-data processing subsystem 40 and display the selective coil sensor data and information, physiological and spatial parameters, physiological characteristics and subject information via a variety of media, such as a PDA, a mobile phone, and/or a computer monitor, etc.

Data Transmission Subsystem

According to the invention, various communication links and protocols can be employed to transmit control signals to the data acquisition subsystem 20 and, hence, paired coils, and coil transmissions (or signals) from the paired coils to the control-data processing subsystem 40. Various communication links and protocols can similarly be employed to transmit data and information, including coil transmissions (or signals) and related parameters, physiological characteristics, spatial parameters, and subject information from the control-data processing subsystem 40 to the data monitoring subsystem 60 of the invention.

In some embodiments of the invention, the communication link between the data acquisition subsystem 20 and the control-data processing subsystem 40 comprises conductive wires or similar direct communication means. In some embodiments, the communication link between the data acquisition subsystem 20 and the control-data processing subsystem 40, as well as between the control-data processing subsystem 40 and data monitoring subsystem 60, comprises a wireless link.

According to the invention, the data transmission subsystem 50 of the invention is programmed and adapted to monitor and control the noted communication links and, hence, transmissions by and between the data acquisition subsystem 20, control-data processing subsystem 40 and data monitoring subsystem 60.

In some embodiments of the invention, the data acquisition subsystem 20 includes at least one, preferably, a plurality of additional physiological sensors that are adapted to monitor and record one or more physiological characteristics associated with the monitored subject. According to the invention, the physiological sensors can include, without limitation, sensors that are adapted to monitor and record electrical activity of the brain, heart, and other muscles (e.g. EEG, ECG, EMG), pulse rate, blood oxygen saturation level (e.g., $SpO_2$), skin temperature, and core temperature. Physiological parameters measured and/or calculated may include, for example, heart rate, respiration rate, blood oxygen level, blood flow, hydration status, calories burned, muscle fatigue, and/or body temperature Exemplary physiological sensors are disclosed in U.S. Pat. No. 6,551,252, U.S. Pat. No. 7,267,652, and co-pending U.S. patent application Ser. No. 11/764,527, filed Jun. 18, 2007, each of which is incorporated by reference herein in its entirety.

According to the invention, the additional sensors can be disposed in a variety of anatomically appropriate positions on a subject. By way of example, a first sensor (i.e., pulse rate sensor) can be disposed proximate the subject's heart to monitor pulse rate and a second sensor (i.e., microphone) can be disposed proximate the throat to monitor sounds emanating therefrom (e.g., sounds reflecting coughing).

As indicated above, the data acquisition subsystem 20 can also include one or more audio sensors, such as a microphone, for monitoring sounds generated by a monitored subject, and a speaker to enable two-way communication by and between the monitored subject and a monitoring station or individual.

According to the invention, the paired coils, e.g., electromagnetic coils 22a, 22b and 24a, 24b, and the aforementioned additional sensors can be positioned on or proximate a subject by various suitable means. Thus, in some embodiments, the paired coils and/or additional sensors are directly attached to the subject.

In a preferred embodiment of the invention, the paired coils, additional sensors, processing and monitoring systems, e.g. LDUs, if employed, are embedded in or carried by a wearable garment or item that can be comfortably worn by a monitored subject. The associated wiring, cabling and other power and signal transmission apparatus and/or systems can also be embedded in the wearable garment.

According to the invention, the wearable monitoring garment can comprise various garments, such as a shirt, vest or jacket, belt, cap, patch, and the like. A suitable wearable monitoring garment, i.e., vest, is illustrated and described in co-pending U.S. Patent Application No. 61/275,576, filed Sep. 1, 2009, co-pending U.S. patent application Ser. No. 12/869,576, filed concurrently herewith, co-pending U.S.

Patent Application No. 61/275,633, filed Sep. 1, 2009, and co-pending U.S. patent application Ser. No. 12/869,627, filed concurrently herewith, each of which is incorporated by reference herein in its entirety.

Additional suitable garments are also disclosed in U.S. Pat. No. 7,267,652, issued Sep. 11, 2007, U.S. Pat. No. 6,551,252, issued Apr. 22, 2003, and U.S. Pat. No. 6,047,203, issued Apr. 4, 2000; each of which is incorporated by reference herein in its entirety.

As set forth in the noted incorporated references, the paired coils or magnetometers, and the aforementioned additional sensors, processing and monitoring systems, LDUs and other equipment can be arranged in or carried by the wearable monitoring garment, for example, in open or closed pockets, or attached to the garment, as by sewing, gluing, a hook and pile system, e.g., VELCRO® such as that manufactured by Velcro, Inc., and the like.

The methods and systems of the invention, described above, thus provide numerous significant advantages over conventional physiology monitoring methods and systems. Among the advantages are the provision of methods and systems that provide (i) accurate, real-time determination of a plurality of physiological characteristics, (ii) accurate determination of a plurality of respiratory parameters and characteristics, (iii) accurate assessment of chest wall movement(s) and the relationship(s) thereof to respiratory activity and respiratory associated events, such as speaking and coughing, (iv) real-time determination and characterization of respiratory events, and (v) real-time determination and characterization of a subject's orientation and movement.

A further significant advantage is the provision of additional and pertinent data that facilitates three-dimensional modeling of chest wall shape and movement of ambulatory subjects.

Another significant advantage of the invention is the provision of systems and associated methods that facilitate evaluation and quantification of ventilatory mechanics, i.e., synchronous and asynchronous movement of the chest wall compartments, and "real-time" three-dimensional modeling of the chest wall. As stated above, this has huge implications in the field of use, as well as applications specific disease states, such as asthma and COPD, and acute disease states, such as pneumo-thorax and pulmonary embolism.

Another advantage of the invention is the provision of systems for accurately determining tidal volume (VT) and other respiratory characteristics that do not require complex calibration algorithms and associated methods. This similarly has huge implications in the field of use, as well as applications for specific disease states, such as COPD.

Yet another advantage of the invention is the provision of monitoring systems that allow for measurement of front to back separation between magnetometers as well as vertical separation between different sets of magnetometers. This allows the system to separate a desired signal and information from motion artifacts caused by ambulatory motion.

Additional advantages and applications of the present invention are apparent with reference to the systems and methods disclosed in U.S. patent application Ser. No. 12/869,578, filed concurrently herewith, U.S. patent application Ser. No. 12/869,576, filed concurrently herewith, U.S. patent application Ser. No. 12/869,585, filed concurrently herewith, U.S. patent application Ser. No. 12/869,592, filed concurrently herewith, U.S. patent application Ser. No. 12/869,627, filed concurrently herewith, U.S. patent application Ser. No. 12/869,625, filed concurrently herewith, and U.S. patent application Ser. No. 12/869,586, filed concurrently herewith, each of which is incorporated by reference herein in its entirety.

Without departing from the spirit and scope of this invention, one of ordinary skill can make various changes and modifications to the invention to adapt it to various usages and conditions. As such, these changes and modifications are properly, equitably, and intended to be, within the full range of equivalence of the following claims.

What is claimed is:

1. A fitness monitoring system for monitoring parameters of a subject engaged in a physical activity, comprising:
   a monitoring garment configured to cover at least a portion of the subject's torso;
   a sensor subsystem including a first sensor, a second sensor, a third sensor, and a fourth sensor, wherein:
   the first, third, and fourth sensors are on the subject's front chest region when the garment is worn by the subject,
   the second sensor is on the subject's back chest region when the garment is worn by the subject,
   the first and second sensors are responsive to changes in distance therebetween,
   the third and second sensors are responsive to changes in distance therebetween,
   the fourth and second sensors are responsive to changes in distance therebetween,
   the sensor subsystem is configured to generate and transmit a distance signal representative of at least the distance between the first and second sensors without initial calibration, and
   the first and second sensors are incorporated into the garment; and
   a processor subsystem in communication with the sensor subsystem and configured to receive the distance signal, wherein the processor subsystem is configured to control the sensor subsystem and to process the distance signal, wherein the processor subsystem includes a programmed algorithm that includes an empirical relationship for determining a respiratory parameter from the distance signal, is adapted to store benchmark respiratory parameter signals, is configured to compare the distance signal with the benchmark respiratory parameter signals, is configured to generate and transmit a respiratory parameter signal representative of the respiratory parameter as a function of the comparison of the distance signal with the benchmark respiratory parameter signals, the processor subsystem includes stored adverse physiological parameters and the processor subsystem is further configured to compare a detected physiological parameter to the stored adverse physiological parameters, and to generate and transmit an adverse physiological parameter signal representative of the adverse physiological parameter associated with the warning signal if the detected physiological parameter corresponds to one of the stored adverse physiological parameters; and
   a data monitoring subsystem programmed and configured to receive the respiratory parameter signal, the data monitoring subsystem being programmed to recognize and display the respiratory parameter associated with the respiratory parameter signal, wherein the processor subsystem is further programmed and configured to generate a three-dimensional model of the subject's chest wall from the magnetometer signal, and wherein the data monitoring subsystem is further programmed and configured to display the generated three-dimensional model of the subject's chest wall.

2. The fitness monitoring system of claim 1, wherein the data monitoring subsystem is configured to receive the respiratory parameter signal, wherein the data monitoring subsystem is programmed and configured to recognize and display the respiratory parameter represented by the respiratory parameter signal.

3. The fitness monitoring system of claim 2 further comprising a transmission subsystem configured to control transmission of the distance signal from the sensor subsystem to the processor subsystem, and the respiratory parameter signal from the processor subsystem to the data monitoring subsystem.

4. The fitness monitoring system of claim 3, wherein the transmission subsystem includes a communication network.

5. The fitness monitoring system of claim 4, wherein the communication network comprises a wireless network.

6. The fitness monitoring system of claim 4, wherein the communication network comprises a wired network.

7. The fitness monitoring system of claim 1, wherein the system includes a physiological monitoring device configured to detect the physiological parameter associated with the subject, the physiological monitoring device being further configured to generate and transmit a physiological parameter signal representative of the detected physiological parameter.

8. The fitness monitoring system of claim 7, wherein the physiological monitoring device is incorporated into the monitoring garment.

9. The fitness monitoring system of claim 1, wherein the processor subsystem is incorporated into the monitoring garment.

10. The fitness monitoring system of claim 4, wherein the transmission subsystem is carried by the garment.

11. The fitness monitoring system of claim 1, wherein the garment comprises a shirt.

12. The fitness monitoring system of claim 1, wherein the garment comprises a vest.

13. The fitness monitoring system of claim 1 further comprising a device for monitoring the subject's movement.

14. The fitness monitoring system of claim 13 further comprising an inertial sensor.

15. The fitness monitoring system of claim 13 further comprising a GPS receiver.

16. The fitness monitoring system of claim 1, wherein, when the garment is worn by the subject, the first sensor is positioned over the sternum of the subject at the level of the fourth intercostal space and the second sensor is placed over the spine at the same level.

17. The fitness monitoring system of claim 1, wherein the sensors comprise magnetometers.

18. The fitness monitoring system of claim 17, wherein the sensors comprise electromagnetic coils.

19. The fitness monitoring system of claim 1, wherein the sensors comprise Hall effect sensors.

20. The fitness monitoring system of claim 1, wherein the sensors comprise electronic compass sensors.

21. The fitness monitoring system of claim 1, wherein the first, third and fourth sensors are positioned on a same axial plane.

22. The fitness monitoring system of claim 1, wherein the first, third and fourth sensors are positioned on different axial planes.

23. A fitness monitoring system for monitoring parameters of a subject engaged in a physical activity, comprising:
a wearable monitoring garment, the monitoring garment being configured to cover at least a portion of the subject's torso;
a magnetometer subsystem including a first magnetometer, a second magnetometer, a third magnetometer, and a fourth magnetometer, wherein:
the first, third, and fourth magnetometers are on the subject's front chest region when the garment is worn by the subject,
the second magnetometer is on the subject's back chest region when the garment is worn by the subject;
the first and second magnetometers are responsive to changes in distance therebetween,
the third and second magnetometers are responsive to changes in distance therebetween,
the fourth and second magnetometers are responsive to changes in distance therebetween,
the magnetometer subsystem is configured to generate and transmit a magnetometer signal representative of at least the distance between the first and second magnetometers without initial calibration, and
the first and second magnetometers are incorporated into the monitoring garment;
a processor subsystem in communication with the magnetometer subsystem, the processor subsystem being programmed and configured to control at least the magnetometer subsystem, the processor subsystem being further configured to receive and process the magnetometer signal, wherein the processor subsystem includes a programmed algorithm that includes an empirical relationship for determining a respiratory parameter from the magnetometer signal, is adapted to store benchmark respiratory parameter signals, is further programmed and configured to generate and transmit a respiratory parameter signal representative of the respiratory parameter when compared to the stored benchmark respiratory parameter signals, and is carried by the monitoring garment; and
a data monitoring subsystem programmed and configured to receive the respiratory parameter signal, the data monitoring subsystem being programmed to recognize and display the respiratory parameter associated with the respiratory parameter signal, wherein the processor subsystem is further configured to generate a three-dimensional model of the subject's chest wall from the magnetometer signal, and wherein the data monitoring subsystem is further programmed and configured to display the generated three-dimensional model of the subject's chest wall.

24. The fitness monitoring system of claim 23 further comprising a spatial parameter sensor configured to detect orientation and motion of the subject, the spatial parameter sensor being further configured to generate and transmit a spatial parameter signal representative of a detected motion of the subject, wherein the processor subsystem is configured to receive and process the spatial parameter signal.

25. The fitness monitoring system of claim 24 further comprising a physiological sensor configured to detect a physiological parameter associated with the subject, the physiological sensor being further configured to generate and transmit a physiological parameter signal representative of the detected physiological parameter, wherein the processor subsystem is configured to receive and process the physiological parameter signal.

26. The fitness monitoring system of claim 23, wherein the processor subsystem is further programmed and configured to determine movement of the subject's chest wall based on the magnetometer signal.

27. The fitness monitoring system of claim 26, wherein the processor subsystem is further programmed and configured to determine a respiratory activity of the subject based on the chest wall movement.

28. The fitness monitoring system of claim 24, wherein the spatial parameter sensor is configured to generate and transmit a spatial parameter signal representative of a detected orientation of the subject.

29. The fitness monitoring system of claim 23, wherein the processor subsystem includes stored adverse physiological parameters and the processor subsystem is further programmed and configured to compare the detected physiological parameter to the stored adverse physiological parameters, and to generate and transmit a warning signal if the detected physiological parameter is one of the stored adverse physiological parameters.

30. The fitness monitoring system of claim 29, wherein the processor subsystem is further programmed and configured to generate and transmit an adverse physiological parameter signal representative of the adverse physiological parameter associated with the warning signal.

31. The fitness monitoring system of claim 24, wherein the processor subsystem includes chest wall parameters, wherein the chest wall parameters have a spatial parameter associated therewith, and wherein the chest wall parameters represent a respiratory parameter and an anatomical parameter.

32. The fitness monitoring system of claim 31, wherein the processor subsystem is further programmed and configured to compare the magnetometer signal and the spatial parameter signal to the chest wall parameters, to select a respective one of the chest wall parameters based on the magnetometer signal and the spatial parameter signal, and to generate and transmit a first chest wall parameter signal representative of the selected chest wall parameter.

33. The fitness monitoring system of claim 23, wherein the system includes an audio sensor configured to detect sounds generated by the subject, the audio sensor being further configured to generate and transmit an audio signal representative of a detected sound generated by the subject.

34. The fitness monitoring system of claim 26, wherein the data monitoring subsystem is further programmed and configured to receive the chest wall signal and display the chest wall movement represented by the chest wall signal.

35. The fitness monitoring system of claim 27, wherein the data monitoring subsystem is further programmed and configured to receive the respiratory activity signal and display the respiratory activity represented by the respiratory activity signal.

36. The fitness monitoring system of claim 31, wherein the data monitoring subsystem is further programmed and configured to receive the chest wall parameter signal and display the chest wall parameter represented by the chest wall parameter signal.

37. The fitness monitoring system of claim 29, wherein the data monitoring subsystem is further programmed and configured to receive the warning signal and display a warning identifying the adverse physiological parameter associated with the warning signal.

38. The fitness monitoring system of claim 23, wherein the system further includes a transmission subsystem configured to control transmission of the magnetometer signal from the magnetometer subsystem to the processor subsystem and to control transmission of signal transmissions from the processor subsystem to the data monitoring subsystem.

39. The fitness monitoring system of claim 38, wherein the transmission subsystem includes a communication network.

40. The fitness monitoring system of claim 39, wherein the communication network comprises a wireless network.

41. The fitness monitoring system of claim 25, wherein the physiological parameter is selected from the group consisting of an electrical activity of the heart, pulse rate, blood pressure, blood oxygen saturation level, skin temperature, EMG, ECG, EEG, and core temperature.

42. The fitness monitoring system of claim 41, wherein the data monitoring subsystem is further programmed and configured to receive the physiological parameter signal and display the physiological parameter represented by the physiological parameter signal.

43. The fitness monitoring system of claim 25, wherein the physiological sensor is incorporated into the monitoring garment.

44. The fitness monitoring system of claim 23, wherein the processor subsystem is incorporated into the monitoring garment.

45. The fitness monitoring system of claim 23, wherein, when the garment is worn by the subject, the first magnetometer is positioned over the sternum of the subject at the level of the fourth intercostal space and the second magnetometer is placed over the spine at the same level.

46. The fitness monitoring system of claim 23, wherein the first, third and fourth sensors are positioned on a same axial plane.

47. The fitness monitoring system of claim 23, wherein the first, third and fourth sensors are positioned on different axial planes.

48. A noninvasive method for monitoring parameters of a subject engaged in a physical activity, comprising:
generating a magnetometer signal representative of at least one of a distance between a first magnetometer and a second magnetometer, a distance between the second magnetometer and a third magnetometer, and a distance between the second magnetometer and a fourth magnetometer, wherein:
the first, second, third, and fourth magnetometers are incorporated into a monitoring garment,
the first, third, and fourth sensors are on the subject's front chest region when the monitoring garment is worn by the subject, and
the second sensor is on the subject's back chest region when the monitoring garment is worn by the subject;
comparing the magnetometer signal with stored benchmark respiratory parameter signals,
determining without initial calibration, with a processor subsystem carried by the monitoring garment that is adapted to store the benchmark respiratory parameter signals, movement of the subject's chest wall as a function of the magnetometer signal and determining, with the processor subsystem, a respiratory activity of the subject as a function of the chest wall movement;
generating a three-dimensional model of the subject's chest wall from the magnetometer signal; and
displaying the generated three-dimensional model of the subjects chest wall.

49. The method of claim 48 further comprising determining a chest wall movement based upon the magnetometer signal.

50. The fitness monitoring system of claim 48, wherein the first, third and fourth sensors are positioned on a same axial plane.

51. The fitness monitoring system of claim 48, wherein the first, third and fourth sensors are positioned on different axial planes.

\* \* \* \* \*